United States Patent
Aoi et al.

(10) Patent No.: US 12,351,830 B2
(45) Date of Patent: Jul. 8, 2025

(54) METHOD FOR MAINTAINING AND AMPLIFYING COLON CANCER STEM CELLS AND METHOD FOR INDUCING COLON CANCER ORGANOID

(71) Applicant: NATIONAL UNIVERSITY CORPORATION KOBE UNIVERSITY, Kobe (JP)

(72) Inventors: Takashi Aoi, Kobe (JP); Ryo Ishida, Kobe (JP); Michiyo Aoi, Kobe (JP); Yoshihiro Kakeji, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 515 days.

(21) Appl. No.: 16/619,455

(22) PCT Filed: Jun. 5, 2018

(86) PCT No.: PCT/JP2018/021624
§ 371 (c)(1),
(2) Date: Dec. 4, 2019

(87) PCT Pub. No.: WO2018/225751
PCT Pub. Date: Dec. 13, 2018

(65) Prior Publication Data
US 2020/0165573 A1    May 28, 2020

(30) Foreign Application Priority Data
Jun. 5, 2017    (JP) .................. 2017-110626

(51) Int. Cl.
*C12N 5/095*    (2010.01)
*C12N 5/00*    (2006.01)
*C12N 5/071*    (2010.01)

(52) U.S. Cl.
CPC ......... *C12N 5/0695* (2013.01); *C12N 5/0062* (2013.01); *C12N 5/0697* (2013.01); *C12N 2501/999* (2013.01); *C12N 2502/1352* (2013.01); *C12N 2502/28* (2013.01)

(58) Field of Classification Search
CPC .. C12N 5/0695; C12N 5/0062; C12N 5/0697; C12N 2501/999; C12N 2502/1352; C12N 252/28
See application file for complete search history.

(56) References Cited

FOREIGN PATENT DOCUMENTS

WO    WO 2015/199088 A1    12/2015

OTHER PUBLICATIONS

Guruswamy et al., S-adenosyl L-methionine inhibits azoxymethan-induced colonic aberrant crypt foci in F344 rats and suppresses human colon cancer Caco-2 cell growth in 3D culture, International Journal of Cancer, 122: 25-30. (Year: 2008).*
Takebe et al., Vascularized and functional human liver from an iPSC-derived organ bud transplant, Nature, 499: 481-485. (Year: 2013).*
Fang et al., Three-dimensional cell cultures in drug discovery and development, 3DD Cell Culture, Drug Screening, and Optimization, 22(5): 456-472. (Year: 2017).*
Sakai et al., Inhibitory effect of FK506 and cyclosporine A on the growth and invasion of human liver cancer cells, The Journal of Medical Investigation, 51: 63-69. (Year: 2004).*
Patankar et al., KRAS and BRAF mutations induce anoikis resistance and characteristic 3D phenotypes in Caco-2 cells, Molecular Medicine Reports, 20: 4634-4644. (Year: 2019).*
Moon et al., Nonsteroidal anti-inflammatory drugs suppress cancer stem cells via inhibiting PTGS2 (cyclooxygenase 2) and NOTCH/HES1 and activating PPARG in colorectal cancer, International Journal of Cancer, 134: 519-529. (Year: 2013).*
Dictionary.com definition of "significant", retrieved from internet Sep. 14, 2023. (Year: 2023).*
Young et al., Organoids as a Model for Colorectal Cancer, Current Colorectal Cancer Reports, 12: 281-297. (Year: 2016).*
Walcher et al., Cancer Stem Cells—Origins and Biomarkers: Perspectives for Targeted Personalized Therapies, Frontiers in Immunology, 11: 1-33. (Year: 2020).*
Roehrl et al., Selective inhibition of calcineurin-NFAT signaling by blocking protein-protein interaction with small organic molecules, PNAS, 101(20): 7554-7559. (Year: 2004).*
Sarabia-Sancjhez, Non-canonical Wnt/Ca2+ signaling is essential to promote self-renewal and proliferation in colon cancer stem cells, Frontiers in Oncology, p. 1-14. (Year: 2023).*
Wang et al., FGF19/SOCE/NFATc2 signaling circuit facilitates the self-renewal of liver cancer stem cells, Theranostics, 11(10): 5045-5060. (Year: 2021).*
Wang et al., FGF19/SOCE/NFATc2 signaling circuit facilitates the self-renewal of liver cancer stem cells, Theranostics, 11(10): 5045-5060, supplement. (Year: 2021).*
Cho et al., Cyclophilin A Inhibitors Suppress Proliferation and Induce Apoptosis of MKN45 Gastric Cancer Stem-like Cells by Regulating CypA/CD147-Mediated Signaling Pathway, International Journal of Molecular Sciences, 24: 1-15. (Year: 2023).*
Silva-Almeida et al., 3D gastrointestinal models and organoids to study metabolism in human colon cancer, Seminars in Cell & Developmental Biology, 98: 98-104. (Year: 2020).*
Strating et al., Co-cultures of colon cancer cells and cancer-associated fibroblasts recapitulate the aggressive features of mesenchymal-like colon cancer, Frontiers in Immunology, p. 01-16. (Year: 2023).*

(Continued)

*Primary Examiner* — Arthur S Leonard
*Assistant Examiner* — Joseph Paul Miano
(74) *Attorney, Agent, or Firm* — Leydig, Voit & Mayer, Ltd.

(57) ABSTRACT

The present invention provides a method for maintenance and expansion of a colon cancer stem cell or induction of a colon cancer organoid. In addition, the present invention provides a medicament screening system using a colon cancer stem cell maintained and expanded or a colon cancer organoid induced by the method.

10 Claims, 16 Drawing Sheets
Specification includes a Sequence Listing.

(56) References Cited

OTHER PUBLICATIONS

Ishida et al., The Tissue-Reconstructing Ability of Colon CSCs Is Enhanced by FK506 and Suppressed by GSK3 Inhibition, Molecular Cancer Research, 15(10): 1455-1466. (Year: 2017).*

Clevers, "The cancer stem cell: premises, promises and challenges," *Nat. Med.*, 17(3): 313-319 (2011).

Dotto, "Calcineurin Signaling as a Negative Determinant of Keratinocyte Cancer Stem Cell Potential and Carcinogenesis," *Cancer Res.*, 71(6): 2029-2033 (2011).

Ishida et al., "The Tissue-Reconstructing Ability of Colon CSCs Is Enhanced by FK506 and Suppressed by GSK3 Inhibition," *Mol. Cancer Res.*, 15(10): 1455-1466 (2017).

Niitsu et al., "*KRAS* mutation leads to decreased expression of regulator of calcineurin 2, resulting in tumor proliferation in colorectal cancer," *Oncogenesis*, 5(8): e253 (2016).

Oshima et al., "Induction of Cancer Stem Cell Properties in Colon Cancer Cells by Defined Factors," *PLoS One*, 9(7): e101735 (2014).

Peuker et al., "Cell-Specific Roles of Calcineurin in Intestinal Tumor Development," *United European Gastroenterology Journal*, 4(5): A17, Abstract OP038 (2016).

Peuker et al., "Epithelial calcineurin controls microbiota-dependent intestinal tumor development," *Nat. Med.*, 22(5): 506-515 (2016).

Werneck et al., "Cyclosporin A inhibits colon cancer cell growth independently of the calcineurin pathway," *Cell Cycle*, 11(21): 3997-4008 (2012).

Zeuner et al., "Colorectal Cancer Stem Cells: From the Crypt to the Clinic," *Cell Stem Cell*, 15(6): 692-705 and Supplemental Information (2014).

Japanese Patent Office, International Search Report in International Patent Application No. PCT/JP2018/021624 (Jul. 24, 2018).

Cao et al., "Effect of Five Novel 5-Substituted Tetrandrine Derivatives on P-glycoprotein-mediated Inhibition and Transport in Caco-2 Cells," *Oncol. Lett.*, 16(5): 6808-6814 (2018).

Shang et al., "Influence of Verapamil on the Pharmacokinetics of Rotundic Acid in Rats and Its Potential Mechanism," *Pharm. Biol.*, 59(1): 198-206 (2021).

* cited by examiner

Fig. 3
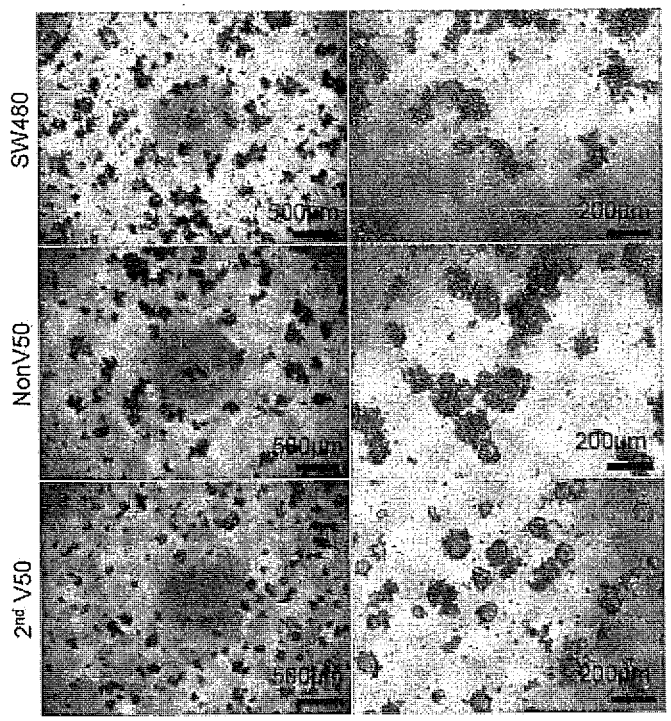
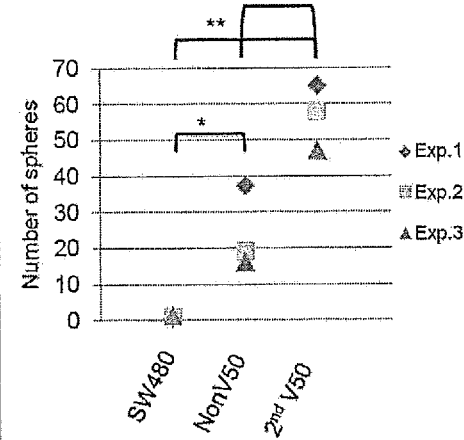
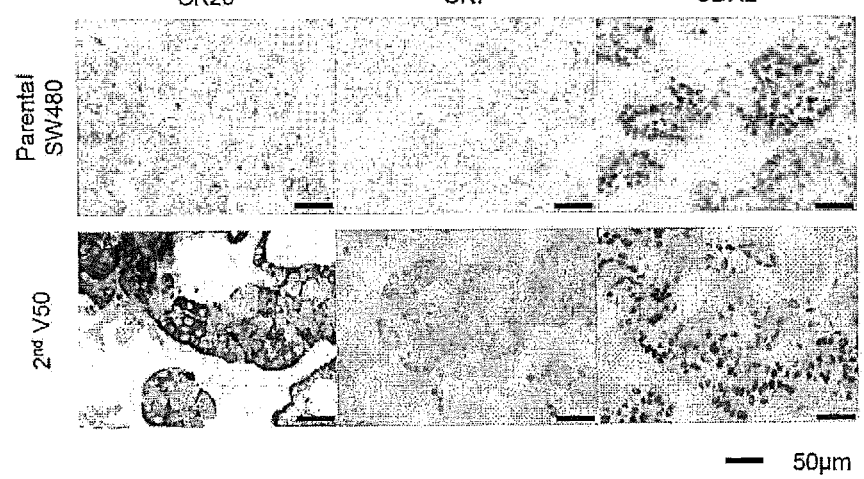

Fig. 9
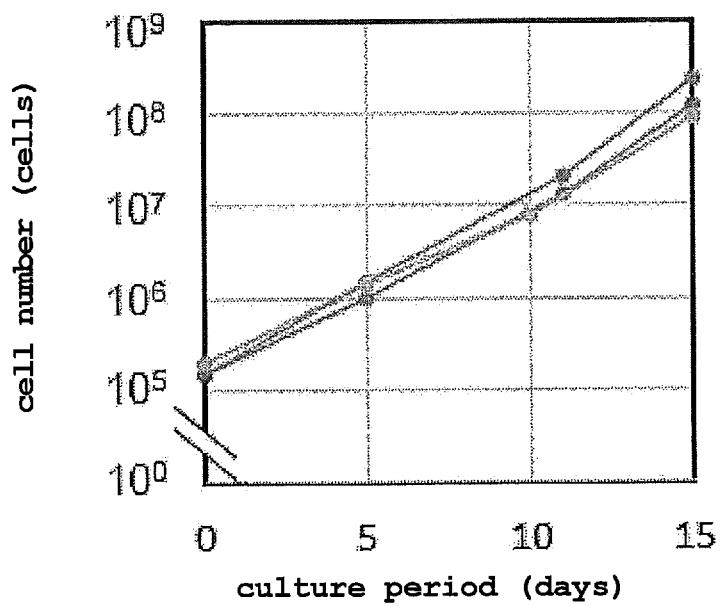
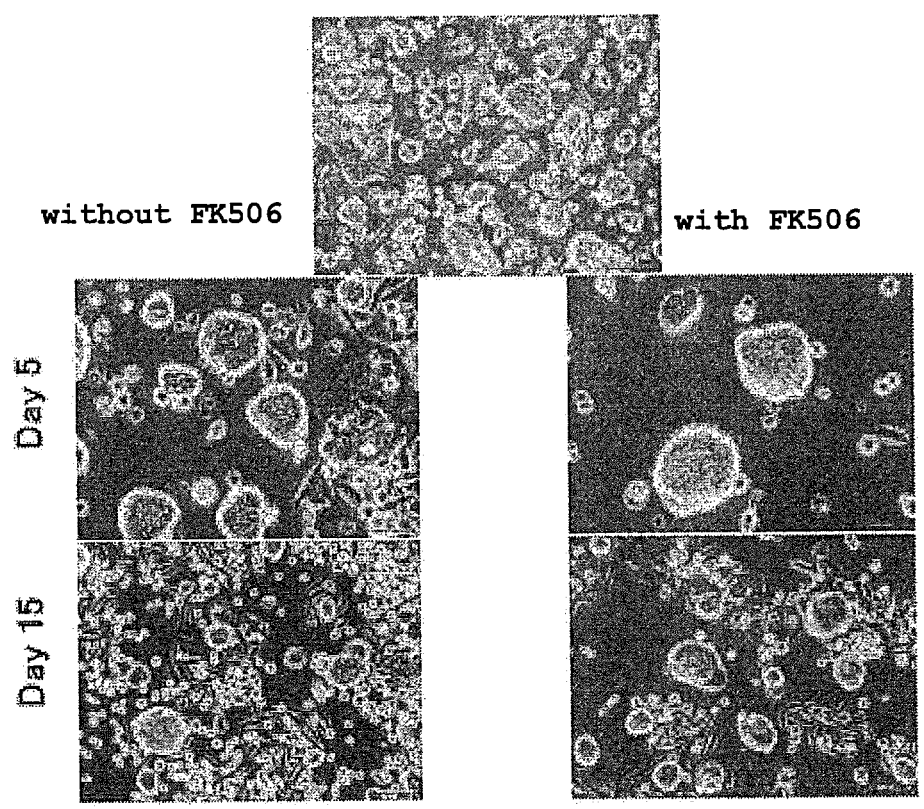

scale bar: 50 μm

METHOD FOR MAINTAINING AND AMPLIFYING COLON CANCER STEM CELLS AND METHOD FOR INDUCING COLON CANCER ORGANOID

CROSS-REFERENCE TO RELATED APPLICATIONS

This patent application is the U.S. national phase of International Patent Application No. PCT/JP2018/021624, filed Jun. 5, 2018, which claims the benefit of Japanese Patent Application No. 2017-110626, filed on Jun. 5, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,891 bytes ASCII (Text) file named "746952SequenceListing.txt," created Dec. 4, 2019.

TECHNICAL FIELD

The present invention relates to a method for maintaining and expanding colon cancer stem cells, and a method for inducing colon cancer organoid. The present invention also relates to a method for screening for an anticancer agent by using the colon cancer stem cells or colon cancer organoid.

BACKGROUND ART

Colon cancer is the 3rd most common malignancy worldwide after lung and breast cancer. Worldwide, nearly 1.4 million patients are diagnosed with and more than 600,000 patients die from colon cancer each year. About half of all such patients develop metastases, and most of these cases have unresectable tumors. Although various drugs, such as chemotherapy and molecular target therapy, have been developed, most of the cases with unresectable tumors cannot be cured.

Recent report suggests that only a subset of cancer cells, called cancer stem cells (CSCs), is capable of reconstructing cancer tissues, thus resulting in both recurrence and metastasis (non-patent document 1), and CSCs are considered to be responsible for the poor prognosis of various types of cancers because of their therapeutic resistance. Therefore, elucidation of the molecular mechanisms of CSCs is very important for the development of CSC-targeting therapies to cure unresectable cancer cases. However, despite various efforts based on such CSC concept, this problem has so far prevented the elucidation of the molecular mechanisms underlying the property of CSCs because of the difficulty of obtaining a sufficient number of CSCs from clinical specimens (non-patent document 2).

On the other hand, the present inventors recently succeed in inducing colon cancer stem-like cells by introducing OCT3/4, SOX2 and KLF4 into some colon cancer cell lines, and named these cells as induced cancer stem cells (iCSCs) (patent document 1, non-patent document 3). Since induced colon cancer stem cell has high medicament eliminating ability compared to the original cancer cells and mimicked well the structure of human colon cancer tissue in vivo, this technique is considered to solve the problem of quantitative limitation on CSC. However, iCSC differentiates into non-stem cell cancer cell that has lost high medicament eliminating ability during maintenance culture, and is diluted more and more since the growth rate of iCSC is significantly lower than that of the non-stem cell cancer cell. To utilize at the initial screening stage for rapidly and conveniently extracting candidate compounds of anti-cancer drugs targeting cancer stem cell from large-scale compound library, it is necessary to build a structure (cancer organoid) similar to human cancer tissue in vitro. However, it remains unclear whether a cancer organoid that stands practical use can be obtained from iCSC.

DOCUMENT LIST

Patent Document patent document 1: WO 2015/199088

Non-Patent Documents non-patent document 1: Clevers H. et al., Nat Med (2011) 17:313-9
non-patent document 2: Zeuner A. et at., Cell Stem Cell (2014) 15:692-705
non-patent document 3: Oshima N. et al., PLoS One (2014); 9:e101735

SUMMARY OF THE INVENTION

Problems to be Solved by the Invention

An object of the present invention is to provide a method for maintaining and expanding colon cancer stem cells or inducing a colon cancer organoid. Another object of the present invention is to provide a screening system for an anti-cancer drug targeting a colon cancer stem cell by using the colon cancer stem cells maintained and expanded by the method or a colon cancer organoid induced by the method.

Means of Solving the Problems

The present inventors have conducted intensive studies in an attempt to achieve the above-mentioned objects and surprisingly found that inhibition of calcineurin, which has been reported to inhibit proliferation of colon cancer cell line in vitro (Peuker K. et al., Nat Med 2016; 22:506-15), promotes tissue reconstructing ability which is the property of colon cancer stem cells. Based on such finding, the present invention has been completed.

That is, the present invention provides the following items.

[1] A method for maintaining and expanding a colon cancer stem cell or inducing a colon cancer organoid comprising culturing the colon cancer stem cell in the presence of a calcineurin inhibitor.
[2] The method of [1], wherein the starting colon cancer stem cell is induced by culturing under conditions where embryonic stem (ES) cells cannot be maintained a colon cancer cell having an exogenous reprogramming factor introduced thereinto.
[3] The method of [2], wherein the starting colon cancer stem cell has a medicament eliminating ability in the presence of an ABC transporter inhibitor at a concentration effective for suppressing a medicament eliminating ability of a colon cancer cell without introduction of an exogenous reprogramming factor.

[4] The method of any of [1] to [3] comprising a step of adhesion-culturing the colon cancer stem cell.

[5] The method of any of [1] to [4] comprising a step of three-dimensional culturing the colon cancer stem cell.

[6] The method of [5], wherein the three-dimensional culture step is performed after the adhesion-culturing step, and one or both of the aforementioned steps is/are performed in the presence of a calcineurin inhibitor.

[7] The method of [6], wherein at least the adhesion culture step is performed in the presence of a calcineurin inhibitor.

[8] The method of any of [5] to [7], wherein the three-dimensional culture step is performed by coculturing a mesenchymal stem/progenitor cell and a vascular endothelial cell.

[9] The method of any of [1] to [8], wherein the calcineurin inhibitor is added for a period of 5-25 days.

[10] The method of any of [1] to [9] wherein the calcineurin inhibitor is FK506.

[11] A method for screening for an anticancer agent, comprising contacting the colon cancer stem cell maintained and expanded or the colon cancer organoid induced by the method of any of [1] to [10] with a test substance and detecting an effect of the test substance on the maintenance or proliferation of the stem cell or the organoid.

[12] A method for screening for an anticancer agent comprising, in the method of any of [1] to [10], performing the culturing in the presence of a calcineurin inhibitor in the co-presence of a test substance, and detecting an effect of the test substance on the maintenance or expansion of the colon stem cell or the induction of the colon organoid.

[13] An agent for inducing maintenance and expansion of a colon cancer stem cell or a colon cancer organoid, comprising a calcineurin inhibitor.

[14] The agent of [13] wherein the calcineurin inhibitor is FK506.

[15] A kit for maintaining and expanding a colon cancer stem cell or inducing a colon cancer organoid, comprising the agent of [13] or [14], and a colon cancer stem cell derived from a colon cancer cell introduced with an exogeneous reprogramming factor and having a medicament eliminating ability in the presence of an ABC transporter inhibitor at a concentration effective for suppressing a medicament eliminating ability of a colon cancer cell without introduction of an exogeneous reprogramming factor.

[16] The kit of [15] wherein the kit is for screening for an anticancer agent.

[17] A colon cancer organoid induced by the method of any of [1] to [10].

Effect of the Invention

According to the method of the present invention, colon cancer stem cells and colon cancer organoids can be produced in large amounts. Using such cells and organoids produced in large amounts, effective and high-throughput screening for an anticancer agent targeting a colon cancer stem cell can be performed and a marker specific to a colon cancer stem cell can be searched for.

BRIEF DESCRIPTION OF THE DRAWINGS

FIG. 3 shows the characteristics of spheres derived from iCSCs. (A) The sphere forming ability in parental SW480 cells, non-V50 cells from $1^{st}$V50-OKS cells and $2^{nd}$ V50-OKS cells is shown. Substantial numbers of spheres are formed in $2^{nd}$ V50-OKS cells. The numbers of spheres of each experiment are shown. (n=3). * p<0.05, ** p<0.01 (B) Histological and immunohistochemical analyses of the spheres of parental SW480 cells and of $2^{nd}$ V50-OKS cells are shown. The spheres derived from parental SW480 cells were negative for CK20, CK7 and positive for CDX2. The spheres derived from $2^{nd}$ V50-OKS cells were positive for CK20, CDX2 and negative for CK7.

FIG. 9 shows the results of expansion culture of induced colon cancer stem cell by the addition of FK506.

DESCRIPTION OF EMBODIMENTS

Figure 1:
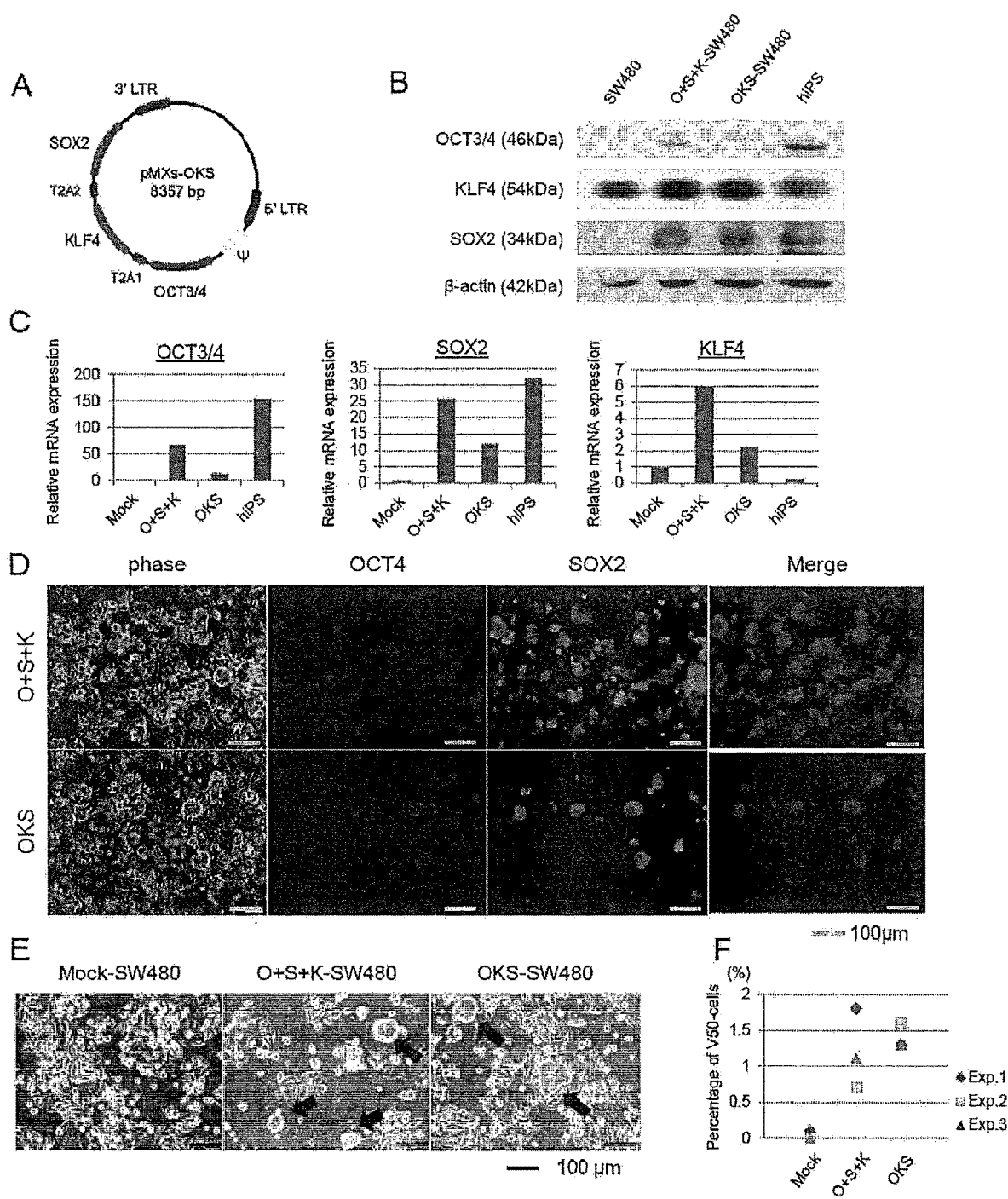
FIG. 1(A) shows a schematic representation of a retroviral polycistronic vector and 2A-linked fusion gene (pMXs-OKS). Three kinds of transcription factors (TFs) (OCT3/4, KLF4 and SOX2) were fused in frame via 2A sequences and coexpressed as a single ORF. (B) Western blotting showing the protein expressions of OCT3/4, SOX2 and KLF4 in SW480 cells transduced with mock, O+S+K and OKS retroviruses and human iPS cells is shown. Cell lysates were collected at 4 days post infection. b-actin was used as an endogenous loading control. (C) QRT-PCR of OCT3/4, SOX2 and KLF4 total transcript levels in transduced SW480 cells at 10 days post infection is shown. The mRNA expression levels were normalized to those of GAPDH. The relative expression levels compared to those of Mock-SW480 are shown. (D) Immunostaining of OCT3/4 and SOX2 in transduced SW480 cells at 10 days post infection is shown. (E) Cell morphologies of O+S+K-SW480 and OKS-SW480 at 10 days post infection are shown. Dome-shaped colonies consisting of cells with unclear edges (arrow) appeared in both transduced SW480 cells, whereas only spindle shape cells were present in Mock-SW480. (F) The V50-cells percentage of each experiment in Mock-SW480 cells, O+S+K-SW480 cells and OKS-SW480 cells is shown.

1. Method for Maintaining and Expanding Colon Cancer Stem Cell or Inducing Colon Cancer Organoid The present invention provides a method for maintaining and expanding a colon cancer stem cell or inducing a colon cancer organoid including culturing a colon cancer stem cell in the presence of a calcineurin inhibitor (hereinafter to be abbreviated as "the method of the present invention").

While the animal from which the colon cancer stem cell is derived is not particularly limited, it is desirably of the same species as the subject of administration of the anticancer agent targeted by the screening method of the present invention. Examples thereof include mammals (e.g., mouse, rat, hamster, guinea pig, dog, monkey, orangutan, chimpanzee, human etc.). In view of the object of the screening method of the present invention, it is preferably human.

In the present invention, the "colon cancer stem cell" means a cell having the ability to reconstruct a colon cancer tissue (hereinafter to be abbreviated as "tissue reconstructing ability"). The colon cancer stem cell to be used in the present invention is not limited as long as a colon cancer tissue can be reconstructed. The colon cancer tissue reconstructing ability can be confirmed by a method known per se. For example, as described in patent document 1, the tissue reconstructing ability can be evaluated by transplanting a colon cancer stem cell into a mouse and evaluating tumor forming ability in vivo. However, as shown in the below-mentioned Examples, the present inventors have found that the sphere forming ability can be used as an index of colon cancer stem cell tissue reconstructing ability. From the aspect of convenience, it is preferable to evaluate the tissue reconstructing ability by the sphere forming ability.

In the present invention, a cancer stem cell can be obtained using the expression of cancer stem cell marker, cell proliferation rate, resistance to anticancer agent, and/or medicament eliminating ability as indices. In the case of, for example, colon cancer stem cell, a cell positive for one or more markers that have been conventionally reported as colon cancer stem cell marker, specifically, at least one marker selected from the group consisting of CD133, CD44, CD26, ABCG2 m and LGR5, can be used as a colon cancer stem cell. Being "positive for a cancer stem cell marker" can be determined by expression of the cancer stem cell marker mRNA in the cells or expression of the cancer stem cell marker protein in the cells. The mRNA of the cancer stem cell marker is not particularly limited and can be confirmed by a method known per se such as RT-PCR method, Northern blot method and the like. The protein of the cancer stem cell marker is not particularly limited and can be confirmed by a method known per se such as Western blot method, immunostaining method and the like. When the cancer stem cell marker is a cell surface antigen marker, it is measured with a flow cytometer to confirm that the cancer stem cell marker is positive.

On the other hand, when cell proliferation rate, resistance to anticancer drugs, and/or medicament eliminating ability is/are used as indices, a cell having properties such as low cell proliferation rate, high resistance to anticancer drugs, and/or high medicament eliminating ability and the like, as compared to general colon cancer cells, can be used as a colon cancer stem cell.

In the present invention, the "maintenance and expansion of colon cancer stem cell" means that the number of cells increases due to cell division while colon cancer stem cells maintain the above-mentioned ability and/or property. In addition, the "colon cancer organoid" means a tissue structure derived in vitro that has a structure similar to that generally observed in natural colon cancer tissues. A sphere with histological characteristics similar to those of typical colon cancer is also included in the colon cancer organoid. Therefore, a method for inducing the colon cancer organoid of the present invention includes a method for forming the sphere from colon cancer stem cells. Examples of the histological characteristics of the above-mentioned typical colon cancer include CK20 positive, CK7 negative and CDX2 positive, which are widely known as histological properties of human colon cancer tissue.

As a method for forming a sphere from colon cancer stem cells, a known method (e.g., Ricci-Vitiani L. et al., Nature 2007; 445:111-51, Sato T. et al., Gastroenterology 2011; 141:1762-72) can be used. Specifically, it can be performed by adding an epidermal growth factor (EGF), a basic fibroblast growth factor (bFGF), insulin, transferrin and/or BSA to a serum-free medium and suspension culturing the cells. The plate to be used here is preferably the Ultra Low Attachment plate (Corning).

Figure 5:
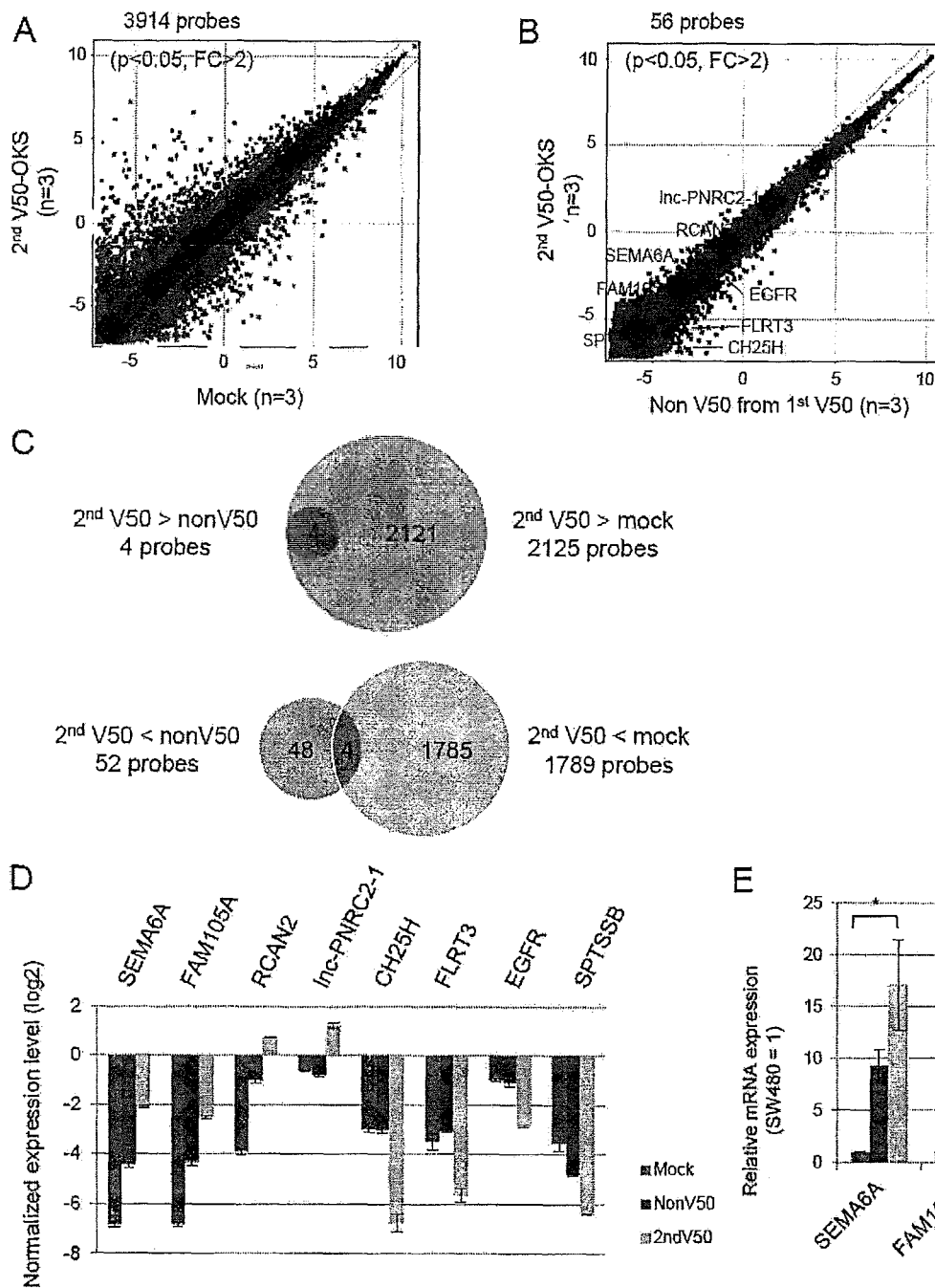
FIG. 5 shows comparison of the gene profiles in the Mock-SW480 cells, nonV50-OKS cells and $2^{nd}$ V50-OKS cells. (A) 3914 probes were identified with significant differences in their expression between Mock-SW480 and $2^{nd}$ V50-OKS cells (t-test, false discovery rate (FDR)<0.05 and two fold differences, shown by gray dots). (B) 56 probes were identified with significant differences in their expression between non-V50 cells from $1^{st}$ V50-OKS cells and $2^{nd}$ V50-OKS cells (t-test, false discovery rate (FDR)<0.05 and two fold differences, shown by gray dots). (C) Venn diagrams of the probes that were more highly expressed in $2^{nd}$ V50 than non-V50, mock, and less expressed in $2^{nd}$ V50 than non-V50, mock are shown. 4 probes each were overlapped in the Venn diagrams. (D) The mRNA expression levels of 8 probes which are overlapped in Venn diagrams are shown (n=3). (E) qRT-PCR of SEMA6A, FAM105A and RCAN2 total transcript levels in parental SW480 cells, non-V50 cells from $1^{st}$ V50-OKS cells and $2^{nd}$ V50-OKS cells 5 days after being sorted (n=3). * p<0.05

As shown in the below-mentioned Example 3 (FIG. 5), from the results of exhaustive gene expression analysis, RCAN2 was identified as one of the genes showing expression levels promoted (i.e., cancer stem cell property and expression level are positively correlated) in the order of parental colon cancer cell line (Mock) transfected with mock vector, non-stem cell cancer cell differentiated after the first sorting (Non V50), and colon cancer stem cell obtained by $2^{nd}$ sorting ($2^{nd}$ V50 cell). RCAN2 was first identified as a thyroid gland hormone response gene in human fibroblasts, but later studies have reported that RCAN2 negatively controls calcineurin (Cao X., et al., Biochem J 2002; 367: 459-66). Thus, the present inventors made a hypothesis that the property of the colon cancer stem cell may be promoted by using a calcineurin inhibitor in culturing the colon cancer stem cell. To verify this, an experiment was performed using a calcineurin inhibitor FK506. As a result, it was verified that the addition of FK506 promotes the property of the colon cancer stem cell. Also, it was verified that a similar result is obtained by the addition of another calcineurin inhibitor cyclosporine A (CsA). As shown in Reference Example 1 described later, inhibition of GSK3, which has a function opposite from the calcineurin's function to promote nuclear transfer of NFAT protein, with various inhibitors suppressed the properties of colon cancer stem cell. Thus, the above-mentioned action of FK506 or cyclosporine A is not specific to FK506 or cyclosporine A but considered to be an action common to calcineurin inhibitors.

Therefore, the property of the colon cancer stem cell can be promoted similarly by using a calcineurin inhibitor other than FK506 and cyclosporine A.

In the present invention, the "calcineurin inhibitor" means a medicament that inhibits some stage of the calcineurin (CaN)-NFAT pathway, or that consequently inhibits the CaN-NFAT pathway by inhibiting or promoting the expression itself of a molecule recruited in the pathway. The "CaN-NFAT pathway" means a series of signal transduction pathways in which calcineurin activated by calcium ion dephosphorylates proteins belonging to the transcription factor NFAT family (hereinafter to be abbreviated as "NFAT"), transfer of dephosphorylated NFAT into the nucleus is promoted, and the NFAT transferred into the nucleus forms a complex with other proteins and activates transcription of NFAT target gene. Examples of the NFAT (nuclear factor of activated T cells) involved in the CaN-NFAT pathway include NFAT1 (also referred to as NFATP or NFATC2, Unigene Hs.356321), NFAT2 (also referred to as NFATC1 or NFATC, Unigene Hs.534074), NFAT3 (also referred to as NFATC4, Unigene Hs.77810) and NFAT4 (also referred to as NFATC3 or NFATX, Unigene Hs.341716).

The calcineurin inhibitor is not particularly limited as long as it can inhibit CaN-NFAT pathway, and includes, for example, FK506 (tacrolimus), cyclosporine A, FK520, pimecrolimus, voclosporin, ascomycin, L685, L818, L732, L731, ISATX247, FK523, 15-0-DeMe-FK-520 and the like. These derivatives and analogs may also be used. For example, WO 2005/087798 describes a cyclosporine derivative that inhibits calcineurin, and WO 2006/078724 describes FK506 and FK520 analogs that inhibit calcineurin. As other calcineurin inhibitors, for example, antibody, peptide aptamer, nucleic acid aptamer that bind to calcineurin or NFAT and inhibit its function, decoy nucleic acid containing the target DNA sequence, which inhibits the binding of NFAT to the target DNA sequence and the like can be mentioned. These inhibitors can be appropriately prepared by a method known per se and using known calcineurin or NFAT protein or a fragment thereof. The decoy nucleic acid can also be chemically synthesized using a DNA/RNA automatic synthesizer based on known NFAT binding sequences (e.g., WO 2010/146622).

Among them, the calcineurin inhibitor used in the present invention is preferably one that specifically inhibits the CaN-NFAT pathway (undesirable off-target effect is sufficiently low). Examples of such inhibitor highly specific for the CaN-NFAT pathway include FK506 and cyclosporine A.

As the substance that inhibits expression itself of a molecule recruited in the CaN-NFAT pathway, antisense nucleic acid, siRNA, shRNA, miRNA, ribozyme and the like for calcineurin or NFAT can be mentioned. A substance that inhibits expression of these can be easily synthesized by appropriately designing by a known design software based on the base sequence of the gene of calcineurin or NFAT family known per se and using a DNA/RNA automatic synthesizer.

When the calcineurin inhibitor is a nucleic acid or protein, it may be introduced into the cell in the form of a nucleic acid or protein, or introduced into the cell using an expression vector expressing same.

The concentration of a calcineurin inhibitor in the medium is not particularly limited as long as maintenance and expansion of colon cancer stem cell is possible or colon cancer organoid can be induced. When FK506 is used, 1-25 µM is preferred and 5-25 µM is more preferred. Also when other calcineurin inhibitor is used, those of ordinary skill in the art can appropriately determine a preferred concentration taking into consideration the above-mentioned concentration of FK506 and technical common knowledge. The period for adding the calcineurin inhibitor to the medium is not particularly limited as long as it can maintain and expand colon cancer stem cell or induce colon cancer organoid. It is preferably not less than 2 days, more preferably not less than 4 days, further preferably not less than 5 days. Also, it is preferable to add a calcineurin inhibitor to the medium for 5 to 25 days.

In the method of the present invention, colon cancer stem cells may be cultured by adhesion culture, three-dimensional culture, or a combination of both culture steps in combination. When the both culture steps are combined, it is preferable to perform adhesion culture of colon cancer stem cells, followed by three-dimensional culture thereof. In this case, one or both of the adhesion culture step and the three-dimensional culture step may be performed in the presence of a calcineurin inhibitor, and at least the adhesion culture step is preferably performed in the presence of a calcineurin inhibitor. Adhesion culture is preferably performed to achieve maintenance and expansion of colon cancer stem cells, and three-dimensional culture is preferably performed to induce colon cancer organoid. In the present invention, the adhesion culture means culturing the target cells or cell aggregate adhered to the bottom surface of the incubator. The three-dimensional culture refers to formation of cell aggregates (sphere, spheroid) by using a low-adhesion culture container or a scaffold such as a porous membrane or hydrogel, and culturing the cells in a three-dimensional state more similar to the state in vivo. The three-dimensional culture is roughly classified into a scaffold type and a scaffold-free type based on the presence or absence of a scaffold. The former is subdivided into a hydrogel type, an inactivated matrix type and the like depending on the kind of the scaffold. As the hydrogel, Matrigel, collagen, laminin and the like derived from animal, plant-derived alginic acid hydrogel and the like, synthetic compound (e.g., OGel™ MT 3D Matrix (Ogel SA), 3-D Life Biomimetic (Cellendes), Puramatrix (3D MATRIX) etc.) can be used. As the inactivated matrix, alvetex (reinnavate), 3D Insert (3D Biotek), VECELL-3D Insert (iwaki) and the like can be used.

Alternatively, scaffold culture can also be performed by loading a porous polystyrene disk into a 96- or 384-well plate or the like. The scaffold-free type is also subdivided into a low-adhesion plate, a micropattern surface plate, a hanging drop method and the like according to the kind of the culture container to be used. A low-adhesion plate is a plate having a bottom surface coated with a hydrophilic polymer to suppress cell adhesion. Examples thereof include PrimeSurface (SUMITOMO BAKELITE CO., LTD.), Ultra-Low Attachment (Corning Incorporated), Nunclon Sphera (Thermo Scientific) and the like. The micro pattern surface plate is a plate having a bottom surface processed to have a micropattern that affects proliferation. Examples thereof include a plate in which only a part of the bottom is adhesive and the cells accumulate there to form an aggregate, a plate in which nanofibers and nanogrids are laid on the bottom to suppress cell adhesion and a cell mass is formed by suppressing planar expansion and the like. The hanging-drop method is a method for forming a cell aggregate in a droplet. For example, a method including forming a cell-containing medium drop at the tip of a chip passed through a hole in a dish, pulling the chip out of the hole to make the drop stay in the hole, and aggregating cells at the bottom of the drop by gravity can be mentioned.

In the present invention, the three-dimensional culture method can be preferably performed by suspension culture. Suspension culture means culturing the target cell or cell aggregate without allowing adhesion to the bottom surface of the incubator. Culturing in a state where cell or cell aggregate is in contact with the bottom surface but the cell or cell aggregate float in the culture medium when the medium is shaken lightly is also encompassed in the suspension culture.

To promote adhesion of the cell to the substrate during adhesion culture, it is preferable to chemically treat the bottom surface of the plastic dish or coat the same with an adhesive coating agent (gelatin, polylysine, agar and the like) that promotes adhesion. During suspension culture, it is preferable to refrain from treating the bottom surface of the plastic dish or coat the same with a coating agent for adhesion prevention (poly(2-hydroxyethylmethacrylate) and the like) that prevents adhesion of the cell to the substrate.

As shown in the below-mentioned Examples, when three-dimensional culture is performed, colon cancer organoid induced from colon cancer stem cell can be induced to a more mature stage by coculture with mesenchymal stem/progenitor cells and interstitial cells such as vascular endothelial cell and the like. Therefore, in a preferable embodiment, the three-dimensional culture step is performed by coculture with interstitial cells containing at least mesenchymal stem/progenitor cells, preferably further containing vascular endothelial cells. Examples of the mesenchymal stem/progenitor cell include stem/progenitor cells derived from bone marrow, adipose tissue, synovium tissue, muscular tissue, peripheral blood, placenta tissue, menstrual blood, cord blood and the like. Examples of the vascular endothelial cell include umbilical vein endothelial cell, microvascular endothelial cell derived from neonatal foreskin, adult skin etc., pulmonary artery vascular endothelial cell, artery vascular endothelial cell, preferably, umbilical vein endothelial cell (particularly, human umbilical vein endothelial cell (HUVEC)).

While the animal from which mesenchymal stem/progenitor cells and vascular endothelial cells are derived is not particularly limited, it is preferably derived from the same species as the animal from which colon cancer stem cell is derived. For example, mammals such as mouse, rat, hamster, guinea pig, dog, monkey, orangutan, chimpanzee, human and the like can be mentioned, and preferred is human.

While the quantitative ratio of mesenchymal stem/progenitor cell and vascular endothelial cell to colon cancer stem cell is not particularly limited, for example, mixed culture at a ratio of colon cancer stem cell:mesenchymal stem/progenitor cell:vascular endothelial cell=10:4:1-5:4:4 can be performed.

The medium to be used in the present invention can be prepared using a medium used for culturing animal cells as a basal medium. Examples of the basal medium include IMDM medium, Medium 199 medium, Eagle's Minimum Essential Medium (EMEM), αMEM medium, Dulbecco's modified Eagle's Medium (DMEM), Ham's F12 medium, RPMI 1640 medium, Fischer's medium, StemPro34 (invitrogen), a mixed medium of these and the like. The medium may contain a serum, or may be serum-free. Where necessary, the medium may contain, for example, one or more serum replacements such as albumin, transferrin, Knockout Serum Replacement (KSR) (serum replacement of FBS during culture of ES cells), N2 supplement (Invitrogen), B27 supplement (Invitrogen), fatty acid, insulin, collagen precursor, trace element, 2-mercaptoethanol (2ME), thiolglycerol and the like, and can also contain one or more substances from lipid, amino acid, L-glutamine, Glutamax (Invitrogen), non-essential amino acid, vitamin, growth factor, low-molecular compound, antibiotic, antioxidant, pyruvic acid, buffering agent, inorganic salts and the like.

The medium to be used in the present invention may be preferably DMEM, DMEM/F12 or DMEM medium containing FBS. The concentration of FBS in the medium is not particularly limited as long as it is a concentration used by those of ordinary skill in the art in general cell culture. For example, it is within the range of 1-30%, preferably 1-20%. The concentration of FBS in the medium is, for example, 1%, 2%, 3%, 4%, 5%, 6%, 7%, 8%, 9%, 10%, 11%, 12%, 13%, 14%, 15%, 16%, 17%, 18%, 19%, 20%, preferably 10%.

The medium used in the present invention may further contain penicillin to prevent bacterium infection. While the concentration of penicillin is not particularly limited as long as it is a concentration used by those of ordinary skill in the art in general cell culture, it is, for example, within the range of 1-500 Units/ml, preferably 1-200 Units/ml. The concentration of penicillin in the medium is, for example, 1 Unit/ml, 25 Units/ml, 50 Units/ml, 60 Units/ml, 70 Units/ml, 80 Units/ml, 90 Units/ml, 100 Units/ml, 110 Units/ml, 120 Units/ml, 130 Units/ml, 140 Units/ml, 150 Units/ml, 175 Units/ml, 200 Units/ml, preferably 100 Units/ml.

The medium used in the present invention may further contain streptomycin to prevent bacterium infection. While the concentration of streptomycin is not particularly limited as long as it is a concentration used by those of ordinary skill in the art in general cell culture, it is, for example, within the range of 1-500 µg/ml, preferably 1-200 µg/ml. The concentration of streptomycin in the medium is, for example, 1 µg/ml, 25 µg/ml, 50 µg/ml, 60 µg/ml, 70 µg/ml, 80 µg/ml, 90 µg/ml, 100 µg/ml, 110 µg/ml, 120 µg/ml, 130 µg/ml, 140 µg/ml, 150 µg/ml, 175 µg/ml, 200 µg/ml, preferably 100 µg/ml.

The culture temperature is, for example, 35-42° C., preferably 36-40° C., more preferably 37-39° C. Culture may be performed in an atmosphere of 2-5% $CO_2$, 5-20% $O_2$. Examples of the culture method include a method of culturing colon cancer stem cell at 37° C. in the presence of 5% $CO_2$ in DMEM medium containing 10% FBS, penicillin and streptomycin and the like.

The derivation of the colon cancer stem cell to be used in the present invention is not particularly limited. It may be a colon cancer stem cell induced by introducing a reprogramming factor into colon cancer cells (i.e., induced colon cancer stem cell; sometimes to be abbreviated as "colon iCSC" or simply as "CSC" in the below-mentioned Examples), or a cell isolated from a culture cell line or cancer tissue in vivo. Preferred is an induced colon cancer stem cell. The induced colon cancer stem cell can maintain a genome mutation characteristic of the original colon cancer cell. Examples of the genome mutation characteristic of the original colon cancer cell include, but are not limited to, mutation of gene such as APC, p53, DCC, K-ras and the like, deletion, translocation, overlapping and substitution of chromosome and the like.

The induced colon cancer stem cell to be used in the present invention induced can be produced by a known method (e.g., the methods described in patent document 1, WO 2011/049099). For example, it can be induced by culturing colon cancer cells, into which an exogenous reprogramming factor has been introduced, under conditions where embryonic stem (ES) cell cannot be maintained. The thus-produced induced colon cancer stem cell can be suitably used in the method of the present invention.

Examples of the reprogramming factor used for the production of induced colon cancer stem cell include a combination of Oct3/4, Sox2 and Klf4. In this case, instead of Oct3/4, other Oct family members such as Oct1A, Oct6 and the like can also be used. Instead of Sox2, other members of the Sox family such as Sox1, Sox3, Sox15, Sox17, and Sox18 can also be used. Instead of Klf4, other members of the Klf family such as Klf1, Klf2, Klf5 and the like can also be used. Furthermore, in addition to Oct3/4, Sox2 and Klf4, any substance may be contained. Any substance to be added is a substance (group) that, when introduced into a somatic cell, transfers the somatic cell to a more undifferentiated state. Examples include, but are not limited to, a gene specifically expressed in ES cells, or a gene that plays a key role in the maintenance of the undifferentiated state of ES cells, or a gene product thereof and the like. Examples of the gene specifically expressed in ES cells, or a gene that plays a key role in the maintenance of the undifferentiated state of ES cells, or a gene product thereof include c-Myc, L-Myc, N-Myc, TERT, SV40 Large T antigen, HPV16 E6, HPV16 E7, Bmil, Lin28, Lin28b, Nanog, Esrrb and Esrrg. Any substance to be added during introduction may be a substance (group) that, when introduced into a somatic cell, increases the efficiency of transferring the somatic cell to a more undifferentiated condition. Examples thereof include, but are not limited to, a substance (group) that promotes establishment efficiency of iPS cells. Examples of the substance (group) that promotes establishment efficiency of iPS cells include, but are not limited to, the following substance (group): histone deacetylase (HDAC) inhibitors [e.g., low-molecular inhibitors such as valproic acid (VPA) (Nat. Biotechnol., 26(7): 795-797 (2008)), trichostatin A, sodium butyrate, MC 1293, and M344, nucleic acid-based expression inhibitors such as siRNAs and shRNAs against HDAC (e.g., HDAC1 siRNA Smartpool (registered trade mark) (Millipore), HuSH 29mer shRNA Constructs against HDAC1 (OriGene) and the like), and the like], DNA methyltransferase inhibitors (e.g., 5'-azacytidine) [Nat. Biotechnol., 26(7): 795-797 (2008)], G9a histone methyltransferase inhibitors [e.g., low-molecular inhibitors such as BIX-01294 (Cell Stem Cell, 2: 525-528 (2008)), nucleic acid-based expression inhibitors such as siRNAs and shRNAs against G9a (e.g., G9a siRNA (human) (Santa Cruz Biotechnology) and the like) and the like], L-channel calcium agonists (e.g., Bayk8644) [Cell Stem Cell, 3, 568-574 (2008)], p53 inhibitors [e.g., siRNA and shRNA against p53 (Cell Stem Cell, 3, 475-479 (2008)), Wnt Signaling activator (e.g., soluble Wnt3a) [Cell Stem Cell, 3, 132-135 (2008)], growth factors such as LIF, bFGF etc., ALK5 inhibitors (e.g., SB431542) [Nat Methods, 6: 805-8 (2009)], a mitogen-activated protein kinase signaling inhibitor, a glycogen synthase kinase-3 inhibitor [PloS Biology, 6(10), 2237-2247 (2008)], miRNAs such as miR-291-3p, miR-294, and miR-295 [R. L. Judson et al., Nat. Biotechnol., 27:459-461 (2009)].

The reprogramming factor can be introduced in the form of DNA or in the form of a protein. When introduced in the form of DNA, it can be introduced using, for example, vectors such as virus, plasmid and artificial chromosome (e.g., human artificial chromosome (HAC), yeast artificial chromosome (YAC), bacterium artificial chromosome (BAC, PAC) etc.) and by methods such as lipofection, liposome method and microinjection. Examples of viral vectors include retrovirus vectors, lentivirus vectors (both Cell, 126, pp. 663-676, 2006; Cell, 131, pp. 861-872, 2007; Science, 318, pp. 1917-1920, 2007), adenovirus vectors (Science, 322, 945-949, 2008), adeno-associated virus vectors, Sendai virus vectors (Proc. Jpn. Acad. Ser. B. Phys. Biol. Sci. 85, 348-62, 2009) and the like. The vectors may contain regulatory sequences such as a promoter, enhancer, ribosome-binding sequence, terminator or polyadenylation site to allow a reprogramming factor to be expressed. Examples of the promoter to be used include EF1α promoter, CAG promoter, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like. Furthermore, the vector may also contain the origins and sequences relating to the replication of lymphotrophic herpes virus, BK virus and bovine papilloma virus, so as to be replicated to exist episomally even in the absence of integration into the chromosome. For example, it may contain EBNA-1 and oriP or Large T and SV40ori sequences (WO 2009/115295, WO 2009/157201 and WO 2009/149233).

To simultaneously introduce multiple reprogramming factors, an expression vector causing polycistronic expression may also be used. For polycistronic expression, sequences encoding the gene may be linked by IRES or a foot-and-mouth disease virus (FMDV) 2A coding region or 2A coding region (T2A) of Thosea asigna virus (Science, 322:949-953, 2008 and WO 2009/092042, WO 2009/152529, PLoS One. 6(4):e18556, 2011). From the aspect of uniform expression of the reprogramming factor, preferred is an expression vector for polycistronic expression.

Microinjection is a method in which a protein solution is placed in a glass needle having a tip diameter of about 1 μm and introduced by puncture into a cell, by which the protein can be certainly introduced into the cell. In addition, protein introduction methods such as electroporation method, semi-intact cell method (Kano, F. et al. Methods in Molecular Biology, Vol. 322, 357-365(2006)), introduction method by Wr-t peptide (Kondo, E. et al., Mol. Cancer Ther. 3(12), 1623-1630(2004)) and the like can also be used.

The colon cancer cell to be used for the production of induced colon cancer stem cell may be a primary cultured cell isolated from an individual, or an established cell line that have acquired the ability to proliferate indefinitely (immortalized) in vitro. Examples of the colon cancer established cell line include HT29, HCT8, HCT116, W620, SW480, SW837, DLD-1, CACO-2, LoVo and the like, and preferred is SW480 cell. The colon cancer cell is preferably derived from human.

The basal medium and medium additive for inducing cancer stem cells in the present invention may be similar to those described above.

In the present invention, as the "maintenance culture conditions of ES cell", for example, conditions for culturing in a medium containing bFGF or SCF, conditions using extracellular matrix (e.g., Matrigel, laminin 511, laminin 332, or fragment thereof) used for aiding maintenance culture, conditions using feeder cell (e.g., mouse embryonic fibroblast (MEF), STO cell (ATCC, CRL-1503)) used for aiding maintenance culture, conditions using culture supernatant of culture of the feeder cell and the like can be mentioned. Under what culture conditions the maintenance culture of ES cell is possible is obvious to those of ordinary skill in the art.

In the present invention, the medium for culturing colon cancer cells introduced with a reprogramming factor is preferably DMEM, DMEM/F12 or DMEM medium containing FBS. The concentration of FBS in the medium is the same as that described above.

The culture temperature is preferably 30-40° C., more preferably 37° C. The $CO_2$ concentration is preferably 2-5%. As an exemplary culture method, a method including introducing a reprogramming factor into a colon cancer cell, for example, and culturing at 37° C. in the presence of 5% $CO_2$ in DMEM medium containing 10% FBS, penicillin and streptomycin can be mentioned. It is preferable to exchange the medium with a fresh medium after lapse of a given period and it is preferable to change the medium after 24 hr from the contact of the colon cancer cell and the reprogramming factor.

It is preferable that the induced colon cancer stem cell used in the present invention have a medicament eliminating ability even in the presence of an ATP binding cassette (ABC) transporter inhibitor at a concentration effective for suppressing the medicament eliminating ability of a colon cancer cell without introduction of an exogeneous reprogramming factor. A cell having a medicament eliminating ability is, for example, SP (Side population) cell, and the SP cell is a cell population that appears in a position (part with dark fluorescence, i.e., "Hoechst Blue slightly positive and Hoechst Red slightly positive") different on the cytogram from the normal cell (cell other than undifferentiated cell) that emits fluorescence at 405 nm and 600 nm when a fluorescent dye called Hoechst33342 is taken into the cell and excited by UV in the analysis by flow cytometry. Therefore, a preferable medicament to be discharged in the present invention is Hoechst33342, and a colon cancer stem cell having a medicament eliminating ability can be extracted using Hoeschst33342 as an index. Therefore, the induced colon cancer cell used in the present invention is preferably an induced colon cancer stem cell (hereinafter to be abbreviated as "$1^{st}$ iCSC") obtained by a step of extracting cells having drug exclusion ability (hereinafter abbreviated as "primary extraction step") under a condition where an ABC transporter inhibitor having a concentration effective for suppressing the medicament eliminating ability of colon cancer cell without introduction of an exogenous reprogramming factor, more preferably a secondary induced colon cancer stem cell (hereinafter to be abbreviated as "$2^{nd}$ iCSC") obtained by performing an extraction step (hereinafter to be abbreviated as "secondary extraction step") similar to the above-mentioned step after culturing $1^{st}$iCSC for a given period. The period from introduction of the reprogramming factor to the primary extraction step is, for example, 6 days-12 days, preferably 10 days. The period from the primary extraction step to the secondary extraction step is, for example, 10 days-20 days, preferably 17 days. When $1^{st}$ iCSC or $2^{nd}$ iCSC is used in the present invention, a cell immediately after the extraction step may be used or a cell after culture for a given period may also be used, and the culture period is preferably 6 days-8 days.

The ABC transporter in the present invention is, for example, a transporter that transports using the hydrolysis energy of ATP, preferably a transporter involved in extracellular transport of anticancer agents such as P-glycoprotein (Pgp/MDR1/ABCB1), MDR-associated protein 1 (MPR1), ABCG2 (BCRP/ABCP/MXR).

In the present invention, the ABC transporter inhibitor is not particularly limited as long as it inhibits the function of the ABC transporter. Examples thereof include VX-710, GF120918, XR9576, fumitremorgin C, Ko143, pantoprazole, flavonoids, estrogens, antiestrogens, Dofequidar Fumarate (MS-209) (Cancer Science Volume 100, Issue 11, pages 2060-2068, November 2009), verapamil, reserpine, zosuquidar (LY335973), ciclosporin A, tamoxifen, quinidine, D-α-tocopheryl polyethylene glycol 1000 succinate, PSC833, phenothiazine, SDZ PSC 833, TMBY, MS-073, S-9788, SDZ 280-446, XR9051. The ABC transporter inhibitor is preferably fumitremorgin C, Ko143, Dofequidar Fumarate, verapamil, reserpine, particularly preferably verapamil.

The concentration of the ABC transporter inhibitor used in the present invention is a concentration effective for suppressing the medicament eliminating ability of colon cancer cell without introduction of a reprogramming factor. For example, when the ABC transporter inhibitor is fumitremorgin C, the concentration is not less than 10 μM, when the ABC transporter inhibitor is Ko143, the concentration is not less than 1 μM, when the ABC transporter inhibitor is Dofequidar Fumarate, the concentration is not less than 5 μM, when the ABC transporter inhibitor is verapamil, the concentration is not less than 50 μM, and when the ABC transporter inhibitor is reserpine, the concentration is not less than 10 μM. More preferably, when the ABC transporter inhibitor is verapamil, the concentration is not less than 50 μM and less than 250 μM (e.g., not more than 240 μM, not more than 230 μM, not more than 220 μM, not more than 210 μM, not more than 200 μM, not more than 190 μM, not more than 180 μM, not more than 170 μM, not more than 160 μM, not more than 150 μM).

Examples of a method for isolating a colon cancer stem cell from cultured cell lines or in vivo colon cancer tissues include sphere formation separation method including serum-free suspension culture of cells to form spheres and concentration of colon cancer stem cells, a separation method by SP fractionation, and a separation method using stem cell surface marker. These methods can be performed in the same manner as described above. As described in WO 2013/035824 A1, a method may also be used in which a cancer tissue derived from a colon cancer patient is transplanted into an immunodeficient mouse, subcultured, and a cancer stem cell is selected from the tumor tissue using LGR5 as an index.

The colon cancer stem cells to be used in the present invention may be in the form of a non-uniform cell population in which differentiated cancer cells other than the cancer stem cell are mixed. Preferred is a uniform cell population consisting only of cancer stem cells. Maintenance culture for in vitro self-replication of the colon cancer stem cell after isolation is difficult. To obtain a uniform cell population consisting only of colon cancer stem cells, for example, it is more desirable to perform the step of extracting cells having the above-mentioned medicament eliminating ability.

2. Screening Method

The present invention provides a method for screening for an anticancer agent by using a colon cancer stem cell maintained and expanded as mentioned above, or an induced colon cancer organoid (hereinafter sometimes to be abbreviated as "expanded colon cancer stem cell and the like") (hereinafter sometimes to be abbreviated as "the screening method of the present invention"). The screening method of the present invention includes, for example, culturing the aforementioned expanded colon cancer stem cell and the like in the presence or absence of a test substance, and then detecting the effect of the test substance on the expanded colon cancer stem cell and the like. Examples of the effect of such test substance include a killing effect on expanded colon cancer stem cell and the like, a colon cancer stem cell proliferation-suppressive effect, a differentiation induction effect on colon cancer stem cell into non-stem cell and the like. Selection of an anticancer agent by examining the killing effect of expanded colon cancer stem cell and the like may be performed by, for example, measuring the viability of the cells and the like when a test substance is added, comparing the viability with that when cultured in the absence of the test substance, and determining that the test substance has an anticancer effect when the viability of the cell decreased by culturing in the presence of the test substance. Selection of an anticancer agent by examining the colon cancer stem cell proliferation suppressive effect may be performed by, for example, measuring the proliferation rate of the cells when a test substance is added, comparing the viability with that when cultured in the absence of the test substance, and determining that the test substance has an anticancer effect when the proliferation rate of the cell decreased by culturing in the presence of the test substance. Selection of an anticancer agent by examining the differentiation induction effect on a colon cancer stem cell into a non-stem cell may be performed by, for example, measuring the expression level of a gene/protein reported as a marker of the aforementioned colon cancer stem cell in a cell population when a test substance is added, comparing the expression level with that when cultured in the absence of the test substance, and determining that the test substance has an anticancer effect when the expression level of the marker of the cancer stem cell in the cell population decreased by culturing in the presence of the test substance.

As other embodiment of the method for screening for an anticancer agent, for example, in the method of the present invention, a method including performing the culturing in the presence of a calcineurin inhibitor in the co-presence of a test substance, and detecting an effect of the test substance on the maintenance or proliferation of the stem cell or the organoid can be mentioned. Examples of the effect of such test substance include a killing effect on expanded colon cancer stem cell and the like, a suppressive effect on the maintenance or proliferation of colon cancer stem cell, a differentiation induction effect on colon cancer stem cell into non-stem cell and the like. These can be verified in the same manner as in the methods used in the aforementioned screening method of present invention.

The test substance to be used in the screening method of the present invention may be any known compound or novel compound and examples thereof include cell extract, cell culture supernatant, microorganism fermentation product, extract derived from marine organism, plant extract, purified protein or crude protein, peptide, non-peptidic compound, synthetic low-molecular compound, natural compound and the like. In the present invention, a test substance can also be obtained using any of many approaches in combinatorial library methods known in the pertinent technical field including (1) biological library method, (2) synthetic library method using deconvolution, (3) "one-bead one-compound" library method, and (4) synthetic library method using affinity chromatography selection. While a biological library method using affinity chromatography selection is limited to peptide library, other four approaches can be applied to peptide, non-peptidic oligomer, and low-molecular compound library of a compound (Lam (1997) Anticancer Drug Des. 12: 145-67). Examples of the synthesis method of a molecule library can be found in the pertinent technical field (DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). A compound library can be prepared as a solution (see Houghten (1992) Bio/Techniques 13: 412-21), bead (Lam (1991) Nature 354: 82-4), chip (Fodor (1993) Nature 364: 555-6), bacterium (U.S. Pat. No. 5,223,409), spore (U.S. Pat. Nos. 5,571,698, 5,403,484 and 5,223,409), plasmid (Cull et al. (1992) Proc. Natl. Acad. Sci. USA 89: 1865-9) or phage (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US-B-2002/103360).

3. Agent for Maintenance and Expansion of Colon Cancer Stem Cell or Induction of Colon Cancer Organoid The present invention provides an agent for maintaining and expanding a colon cancer stem cell or inducing a colon cancer organoid containing a calcineurin inhibitor (hereinafter to be abbreviated as "the agent of the present invention").

As the calcineurin inhibitor to be used for the agent of the present invention, those exemplified in the above-mentioned 1 can be mentioned. Among them, FK506 or cyclosporine A is preferred.

The agent of the present invention may contain components other than the calcineurin inhibitor as long as the effect provided by the agent of the present invention is not impaired. Examples of other component include known carrier, such as excipient, diluent, filler, binder, lubricant, fluidizing auxiliary, disintegrant, surfactant, preservative and the like. Examples of the excipient include sugars such as sucrose, trehalose, raffinose, mannitol, dextran and the like, amino acids such as arginine, histidine, glycine, serine, proline and the like, and the like.

In addition, a calcineurin inhibitor for use in the maintenance or proliferation of the stem cell or induction of the organoid is also provided. As the calcineurin inhibitor, those exemplified in the above-mentioned 1 can be mentioned. Among them, FK506 or cyclosporine A is preferred.

4. Kit for Maintenance and Expansion of Colon Cancer Stem Cell or Induction of Colon Cancer Organoid The present invention also provides a kit for maintaining and expanding a colon cancer stem cell or inducing a colon cancer organoid comprising the agent of the present invention and a induced colon cancer stem cell (hereinafter to be abbreviated as "the kit of the present invention").

The induced colon cancer stem cell to be used for the kit of the present invention is as mentioned above. Preferred is a colon cancer stem cell derived from a colon cancer cell having an exogenous reprogramming factor introduced thereinto and having a medicament eliminating ability in the presence of an ABC transporter inhibitor at a concentration effective for suppressing a medicament eliminating ability of a colon cancer cell without introduction of an exogenous reprogramming factor. The kit of the present invention may contain other reagents as necessary in addition to the aforementioned agent of the present invention and induced colon cancer stem cell. As the reagents, those exemplified in the above-mentioned 1 can be similarly mentioned. Examples thereof include, but are not limited to, media (e.g., basal medium, medium additive and the like) for the maintenance and expansion of induced colon cancer cell or induction of colon cancer organoid, ABC transporter and Hoechst33342. The kit of the present invention can also be used for the above-mentioned screening method.

The present invention is explained in more detail in the following by referring to Examples. It is needless to say that the present invention is not limited thereto.

Example

In the below-mentioned Examples, experiments were performed as follows.

<Cell Culture>

A human colon cancer cell line (SW480) and Plat-A amphotropic retrovirus packaging cells were obtained from the ATCC collection and Cell Biolabs (San Diego, CA, USA), respectively. Both cells were maintained in Dulbecco's modified Eagle's medium (DMEM) (Nacalai Tesque, Kyoto, Japan) supplemented with 10% fetal bovine serum (FBS) (Life Technologies) and penicillin (100 Units/ml) and streptomycin (100 μg/ml) (Life Technologies) at 37° C. in a humidified 5% $OO_2$ incubator. In Plat-A culture, 1 μg/ml of puromycin (Nacalai Tesque) and 10 μg/ml of blasticidin (Funakoshi) were added. HUVECs (Lonza) and human MSCs (Lonza) were maintained in endothelial growth medium (Lonza) at 37° C. in a humidified 5% $CO_2$ incubator. The cells were treated with FK506 (Sigma, 25 μM), VPA (WAKO, 1 mM) or CHIR99021 (Funakoshi, 3 μM) for 5 days. Thereafter, the cells were detached from the culture dish by an enzyme treatment, dispersed and the number of the cells was counted with Countess system (Invitrogen). The human induced pluripotent stem (hiPS) cells used as a control were generated from human peripheral blood mononuclear cells in the laboratory.

<Retroviral Infection>

Retroviral vectors separately encoding OCT3/4, SOX2 or KLF4 in pMXs based vectors (pMXs-OCT3/4, pMXs-SOX2, pMXs-KLF4) were obtained from Addgene. Therefore, using these vectors, the polycistronic retroviral vector encoding OCT3/4, KLF4 and SOX2 (pMXs-OKS) was designed. That is, human OCT3/4, KLF4 and SOX2 were amplified by polymerase chain reaction (PCR) with primers containing the 2A sequences of Thosea asigna virus (T2A) and cloned into EcoRI site of pMXs vector using the In-fusion HD cloning system (Clontech). To generate pMXs-NFATc3-GFP construct, NFATc3-GFP cDNA were PCR amplified using HA-NFAT4 (3-407)-GFP (purchased from Addgene #21664) as a template and cloned into EcoRI-NotI site of pMXs-vector).

One day before transfection, Plat-A packaging cells were seeded at 1×10$^6$ cells per 60 mm dish. On the next day, the cells were transfected with 3 μg of pMXs vectors using the Fugene HD transfection reagent (Promega) according to the manufacturer's instructions. Twenty-four hr after transfection, the Plat-A medium was replaced. SW480 was seeded at 7×10$^5$ cells per 60 mm dish. After 24 hr, virus-containing supernatants derived from these Plat-A cultures were filtered through a 0.45 mm cellulose acetate filter (Whatman), supplemented with 4 μg/ml polybrene (Nacalai Tesque), and a mixture of equal amounts of pMXs-OKS virus-containing supernatant or pMXs-OCT3/4, pMXs-SOX2, and pMXs-KLF4 virus-containing supernatant was rapidly added to the target cell. After 24 hr to 36 hr from infection, the virus-containing medium was replaced with a fresh medium.

<Culture of Cells after Introduction of Reprogramming Factor, Isolation of Colon Cancer Stem Cell-Enriched Cell Population and Induction of Colon Cancer Organoid>

Figure 6:
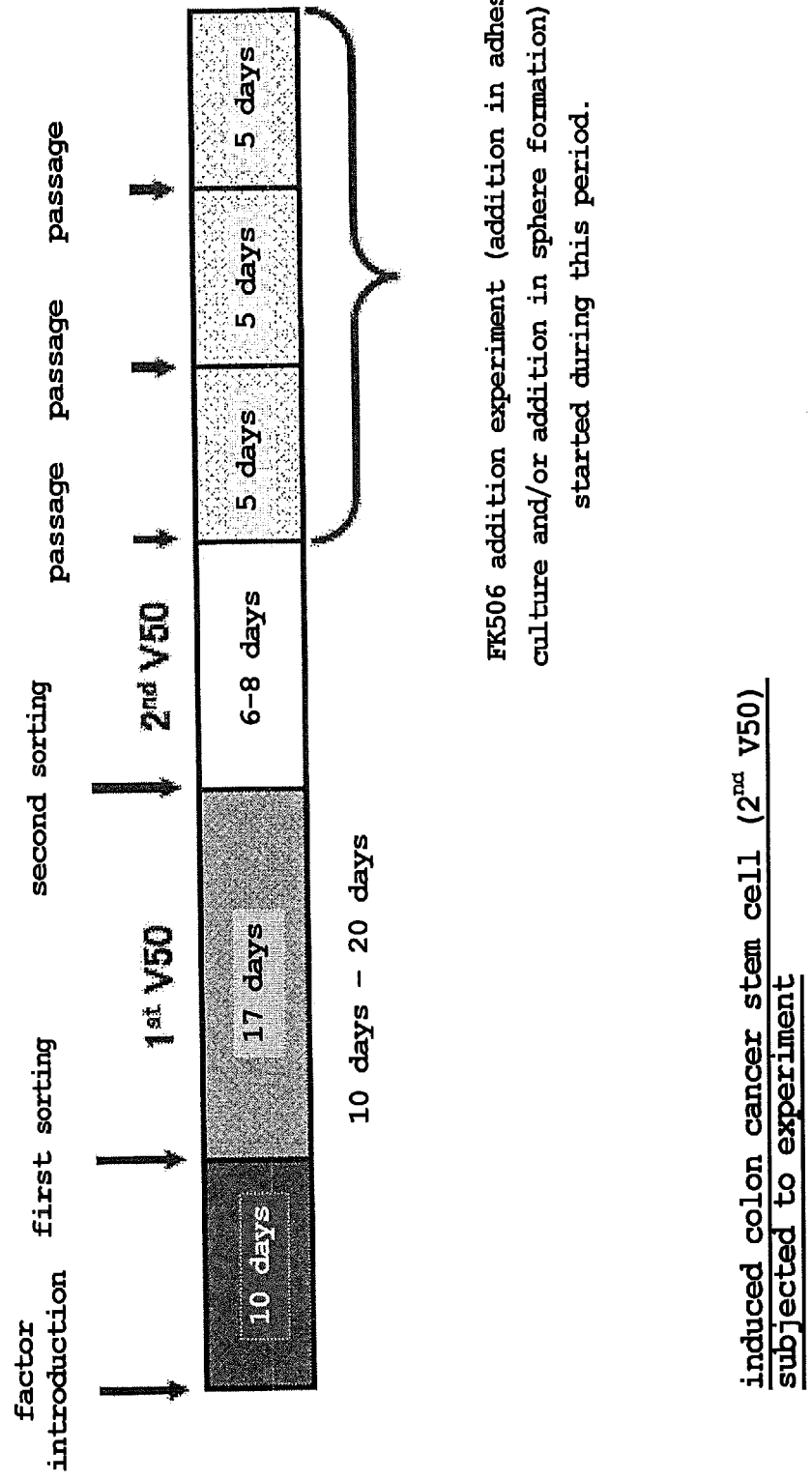
FIG. 6 is a schematic diagram showing a series of flow from introduction of the reprogramming factor to the start of addition of FK506 in FK506 addition experiment.

Culture of SW480 cells after introduction of reprogramming factor, isolation of induced colon cancer stem cell (hereinafter to be also referred to as "colon iCSC")-enriched cell population and induction of colon cancer organoid were performed according to the schedule described in FIG. 6. Establishing culture of colon iCSC and sorting of colon iCSC-enriched cell population were performed according to the method described in the above-mentioned non-patent document 3 (flow cytometry utilizing Hoechst33342 eliminating ability in the presence of 50 μM verapamil). Hereinafter colon iCSC-enriched cell population (cell population not labeled with Hoechst33342 in the presence of 50 μM verapamil; V50 cell) obtained by the first sorting is sometimes to be abbreviated as $1^{st}$ V50 cell (or $1^{st}$ V50-OKS cell), and the V50 cell obtained by the second sorting is sometimes to be abbreviated as $2^{nd}$ V50 cell (or $2^{nd}$ V50-OKS cell). On the other hand, the cell population labeled with Hoechst33342 in the presence of 50 μM verapamil is sometimes to be abbreviated as non V50cell or non V50-OKS cell. Colon cancer organoid was induced by the method described in the below-mentioned sphere formation assay.

<RNA Isolation and Quantitative Reverse-Transcriptase Polymerase Chain Reaction>

Total RNA of the cell was extracted using Trizol (Life Technologies). 500 ng of RNA was reverse transcribed into cDNA using the Prime Script™ II $1^{st}$ strand cDNA Synthesis Kit (Takara) and quantitative PCR analysis was performed in the Light Cycler (registered trade mark) 480 Real time PCR system (Roche) with SYBR (registered trade mark) Premix Ex Taq™II (Takara). PCR primers are listed in Table 1.

TABLE 1

| primer name | sequence (5' → 3') | SEQ ID NO: |
| --- | --- | --- |
| hGAPDH forward | agccacatcgctcagacac | 1 |
| hGAPDH reverse | gcccaatacgaccaaatcc | 2 |
| hOCT3/4 forward | gcgactatgcacaacgagag | 3 |
| hOCT3/4 reverse | cagtttgaatgcatgggaga | 4 |
| hKlf4 forward | catgccagaggagcccaagccaaagagggg | 5 |
| hKLF4 reverse | cgcaggtgtgccttgagatgggaactcttt | 6 |
| hSOX2 forward | ttcacatgtcccagcactaccaga | 7 |
| hSOX2 reverse | tcacatgtgtgagagggcagtgtgc | 8 |
| ABCG2-2 forward | cacaaggaaacaccaatggct | 9 |
| ABCG2-2 reverse | acagctccttcagtaaatgcc | 10 |
| LGR5 forward | gatgttgctcagggtggact | 11 |
| LGR5 reverse | tttcccgcaagacgtaactc | 12 |
| SEMA6A total forward | aggaatgctggactggaagc | 13 |
| SEMA6A total reverse | ggtcgtggcctttgaggtaa | 14 |

TABLE 1-continued

| primer name | sequence (5' → 3') | SEQ ID NO: |
| --- | --- | --- |
| FAM105A total forward | ggcacaagctgaaatggtgg | 15 |
| FAM105A total reverse | tcagcttgttacggggtgtc | 16 |
| RCAN2 total forward | caaactgcacttggctccac | 17 |
| RCAN2 total reverse | cacttggggtggactcagtc | 18 |
| GSK3α forward | aaggctctccccactagagg | 19 |
| GSK3α reverse | gaggagggatgagaatggcg | 20 |
| GSK3β forward | gcagcaaggtgacaacagtg | 21 |
| GSK3β reverse | ttgatggcgaccagttctcc | 22 |

<Western Blotting>

The cells were lysed with the M-PER Mammalian Protein Extraction Reagent (Thermo Fisher Scientific). The cell lysates were subjected to SDS-polyacrylamide gel electrophoresis (SDS-PAGE). After the electrophoretic transfer of the proteins, immunoblotting with mouse anti-OCT3/4 antibody (BD Transduction Laboratories™), rabbit anti-KLF4 antibody (abcam), and goat anti-SOX2 antibody (abcam), mouse anti-β-actin antibody (Sigma Aldrich) followed by horseradish peroxidase (HRP)-conjugated secondary antibodies, was performed. The LAS 3000 imaging system (Fuji Film) was used to detect signals.

<Immunohistochemistry>

The cultured cells were fixed with 4% paraformaldehyde. Mouse anti-OCT3/4 antibody (611202, dilution 1:200, BD transduction Laboratories™) and goat anti-SOX2 antibody (sc-17320, dilution 1:100, Santa Cruz) were used as primary antibodies. For immunofluorescence, fluorophore-conjugated (Alexa Fluor 488, Alexa Fluor 594) secondary antibodies were used to visualize the signal.

<Dye Efflux Activity Analysis>

A dye efflux activity analysis was performed according to known method (Zhou S. et al., Nat Med 2001; 7:1028-34, Patrawala L. et al., Cancer Res 2005; 65:6207-19). The cells were incubated in DMEM containing 2% FBS and 1 mM HEPES with Hoechst33342 (Life Technologies) at 5 μg/ml with or without the co-administration of verapamil (Sigma-Aldrich) at 50 or 250 μM for 90 minutes at 37° C., and were gently inverted every 30 minutes. After incubation, the cells were re-suspended in PBS containing 2% FBS and 1 mM HEPES. The cells were counterstained with 2 μg/ml PI to label dead cells, and were passed through a 35 μm mesh filter, keeping them on ice for flow cytometry and sorting. The cells were analyzed and sorted by a FACS Aria III instrument (BD Bioscience). The Hoechst dye was excited with a violet laser (405 nm), and the fluorescence was measured with both a 450/40 filter (Hoechst Blue) and a 610/20 filter (Hoechst Red).

<5-FU-Chemoresistance Analysis>

A total of $6 \times 10^4$ cells were seeded in 12-well plates with DMEM containing 0, 1, 50 μg/ml of 5-fluorouracil (5-FU, Kyowa Kirin) respectively. After incubation for 72 hr, the cell viability after 5-FU exposure was measured by the Countess (Invitrogen) system.

<Cell Cycle Analysis>

The paraformaldehyde-fixed, permeabilized cells were stained with Hoechst33342 for 5 min at 37° C., then the cells were analyzed by FACS Aria III (Henderson L, et al., Am J Physiol Cell Physiol 2013, 304:C927-38).

<Sphere Formation Assay>

The cells were transferred to Ultra Low Attachment plates (Corning) in serum-free DMEM containing 10 ng/ml bFGF (WAKO), 10 μg/ml human insulin (CST), 100 μg/ml human transferrin (Roche) and 100 μg/ml BSA (Nacalai Tesque), and incubated at 37° C. in a 5% $CO_2$ incubator for 10 days. The sphere count was calculated based on the sphere size which was larger than 100 μm. FK506 (25 μM), VPA (1 mM) or CHIR99021 (3 μM) were added to the medium and the spheres were then treated for 10 days.

<Co-Culture with HUVEC and MSC>

$5 \times 10^5$ parental SW480 cells or iCSCs with $5 \times 10^4$ HUVECs and $2 \times 10^5$ MSCs were resuspended in the sphere forming medium and plated on a low attachment 24-well flat plate (Prime Surface(registered trade mark) 24F, Sumitomo Bakelite). After 10 days, the sphere of collective cells was pathologically analyzed.

<Histological and Immunohistochemistry Analyses of the Spheres>

The spheres were embedded in paraffin blocks, and sectioned at 5-μm in thickness. The sections were deparaffinized and stained with Hematoxylin and Eosin (HE), anti-human cytokeratin 20 (CK20) mouse monoclonal antibody (Clone: Ks20.8, dilution 1:50, Dako), anti-human cytokeratin 7 (CK7) mouse monoclonal antibody (Clone: OV-TL 12/30, dilution 1:50, Dako), anti CDX2 mouse monoclonal antibody (CM226, dilution 1:50, Biocare Medical), anti Ki67 mouse monoclonal antibody (Clone: MIB-1, dilution 1:50, Dako), anti aSMA mouse monoclonal antibody (Clone: 1A4, dilution 1:50, Dako), and anti CD31 mouse monoclonal antibody (Clone: JC70A, dilution 1:50, Dako). Immunohistochemistry was performed using the Benchmark XT (Roche) autostainer with the XT ultraView Universal DAB Detection Kit (Ventana Medical Systems, Inc).

<Microarray Analysis>

The RNA of the Mock-SW480 cells, non-50 cells from $1^{st}$ V50-OKS cells and $2^{nd}$ V50-OKS cells that were collected 5 days after being sorted. The gene expression profiling was carried out using the SurePrint G3 human GE microarray (Agilent Technologies) according to the manufacturer's protocol. The data were analyzed using the GeneSpring 13.0 software program (Agilent Technologies). The data processing was performed as follows: (i) Threshold raw signals were set to 1.0, (ii) log base 2 transformation was performed, and (iii) 75th percentile normalization was chosen as the normalized algorithm (http://genespringsupport.com/faq/normalization). The flag setting was performed as follows: The feature are not positive and significant (not detected), not uniform (compromised), not above background (not detected), saturated (compromised), or is a population outlier (compromised). Control probes were removed and only the "detected" probes that were present in at least one sample in all samples were used for further analysis. The number of probes used in the analysis was 50,739.

<Addition of FK506>

SW480 cells or $2^{nd}$ V50 cells were subjected to flat plane adhesion culture in the presence of FK506 (Sigma) for 5-15 days, and the cell number was counted with Countess (Invitrogen) system. Alternatively, the cells were subjected to flat plane adhesion culture in the presence of FK506, and then suspension culture in the presence or absence of FK506 to form spheres. The sphere number was counted with Countess (Invitrogen) system. Unless otherwise specified, FK506 was used at a concentration of 25 μM in this Example.

<Statistical Analysis>

All data were analyzed using the jstat software program. The data values were presented as the mean±standard error of the mean (SEM) of three independent experiments. The differences in the mean values between two groups were analyzed using the two-tailed paired t-test. The differences were considered to be statistically significant for P-values<0.05 (*) and <0.01 (**).

<siRNA Transfection>

Duplexed Stealth siRNA (Invitrogen) were used for reference examples and were transduced to the cells according to the manufacturer's protocol. The siRNA sequences used were as follows:

```
                                            (SEQ ID NO: 23)
    GSK3a - CCAAGGCCAAGUUGACCAUCCCUAU;

(SEQ ID NO: 24)
    GSK3b - GCUCCAGAUCAUGAGAAAGCUAGAU;

RCAN2-HSS#173486;
                                            (SEQ ID NO: 25)
    SCRAMBLED - AAUUCUCCGAACGUGUCACGUGAGA.
```

<Colony Formation Assay>

$2^{nd}$ VP50 cells produced by 3 independent experiments were seeded in a 6 well plate at a density of $2 \times 10^3$ cells/well. The next day, the medium was changed to a medium not added with the compound, or a medium added with 1 mM VPA, 3 μM CHIR or 25 μM FK506. Thereafter, the medium was changed every 2 days or 3 days. On day 12, the cells were fixed with methanol, stained with crystal violet and the colonies were counted using a stereoscopic microscope.

Example 1: Generation of iCSCs Using a Polycistronic Retroviral Expression Vector Carrying Three Transcription Factors (TFs) from a Colon Cancer Cell Line In a previous study (non-patent document 3), three viral vectors which separately carried OCT3/4, SOX2 or KLF4 to generate the iCSCs from a SW480 human colon cancer cell line were used. Therefore, the transduced cells included various populations that harbor all, two, one or none of the three viral vectors. To avoid heterogeneity, which could hinder the identification of the molecular signature of the iCSCs, a polycistronic retroviral vector in which the three cDNAs encoding OCT3/4, KLF4 and SOX2 were connected with the T2A sequences (pMXs-OKS) was constructed (FIG. 1A).

It was then verified that the OKS fusion gene product can be processed efficiently into the individual proteins. Retroviruses were produced by transfecting this polycistronic vector into PLAT-A packaging cells and then transfected into SW480 cells (OKS-SW480). Using SW480 cell transfected with mock vector (Mock-SW480) was used as a negative control and SW480 cell transfected with a mixture of pMX-OCT3/4, pMX-SOX2 and pMX-KLF4 (O+S+K-SW480) was used as a positive control. A Western blot analysis showed that OCT3/4, KLF4 and SOX2 proteins were detected at the appropriate molecular weight in both OKS-SW480 and O+S+K-SW480 cells, although the KLF4 expression levels did not change substantially, in comparison to the Mock-SW480 cells (FIG. 1B). Quantitative reverse transcription polymerase reaction (qRT-PCR) showed that the total O(OCT3/4), K(KLF4), S(SOX2) transcript levels were also elevated in OKS-SW480 cells (FIG. 1C). In addition, as expected, an immunofluorescence staining analysis showed that almost all of the OKS-SW480 were double positive or double negative for OCT3/4 and SOX2, whereas the OCT3/4- or SOX2-single positive cells were prominent in the O+S+K-SW480 (FIG. 1D).

Next, whether the OKS-SW480 show phenotypes which are similar to those in the previous report using O+S+K-SW480 (non-patent document 3) was evaluated. In the previous report, it was demonstrated that dome-shaped colonies consisting of cells with unclear edges appeared in the O+S+K-SW480 culture, and that the O+S+K-SW480 showed enhanced CSC properties including the marker gene expression, a higher percentage of the cells in the G1/G0 phase and resistance to 5-FU. In addition, it was found that the O+S+K-SW480, but not the Mock-SW480, contained a subset of cells that were unlabeled by Hoechst33432 dye, even in the presence of 50 µM of Verapamil (VM), an ATP-Binding Cassette (ABC) transporter inhibitor, and the V50-cells exhibited the CSC properties. As a result, it is considered that the iCSCs were therefore enriched in the V50-cells.

Figure 2:
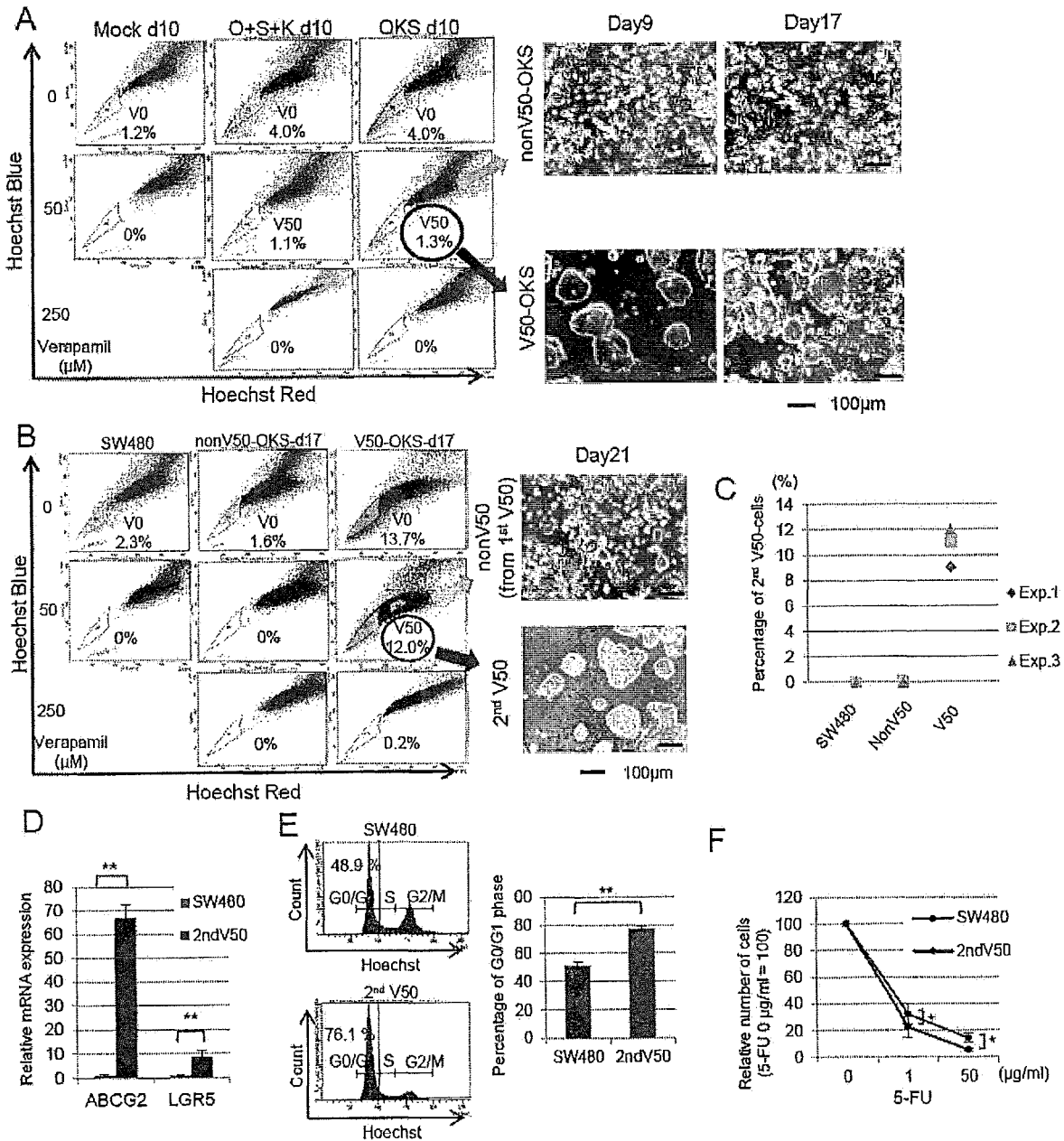
FIG. 2 shows production of induced colon cancer stem cells. (A) A population of cells unlabeled by 5 μg/ml of Hoechst33342 with the co-administration of 50 μM of verapamil (VM) was induced in the OKS-SW480 cells, the same as in the O+S+K-SW480 cells. The cells unlabeled by Hoechst33342 without VM and with 50 μM of VM were designated as V0-cells and V50-cells, respectively. The V50-cells were collected by the cell sorter. The mounted colony shape was enhanced in the V50-cells, whereas the spindle cells were gradually occupied during a long culture. (B) V50-cells were present at a higher rate in the first V50-OKS-cell cultures. This population was sorted and called $2^{nd}$ V50-OKS cells (hereinafter sometimes to be simply referred to as "$2^{nd}$ V50 cell"). (C) The $2^{nd}$ V50 cells percentage of each experiment in parental SW480 cells, non-V50-OKS cells and V50-OKS cells. (D) $2^{nd}$ V50-OKS-SW480 cells had significantly higher mRNA expression levels of ABCG2 and LGR5 compared to the parental SW480 cells. The mRNA expression levels were normalized to those of GADH. The relative expression levels compared to those of parental SW480 are shown (n=3).  p<0.01 (E) The percentage of cells in the G1/G0 phase was significantly higher in $2^{nd}$ V50-OKS cells than that of the parental-SW480 (n=3).  p<0.01 (F) The viability of $2^{nd}$ V50-OKS-SW480 cells in the presence of 5-FU was significantly higher than that of parental SW480 cells at both the 1 and 50 μg/ml concentrations of 5-FU. The relative number of cells with 5-FU compared to those without 5-FU are shown (n=3). * p<0.05

Ten days after transfection, dome-shaped colonies consisting of cells with unclear edges appeared in the OKS-SW480 cultures as well as in the O+S+K-SW480 cultures (FIG. 1E). The proportions of V50-cells in the Mock-SW480, O+S+K-SW480 and the OKS-SW480, were 0%±0.1%, 1.2%±0.3 and 1.4%±0.1, respectively (FIG. 2A, FIG. 1F). Almost all of the sorted V50-cells from OKS-SW480 (V50-OKS) formed dome-shaped colonies, whereas the sorted non-V50 cells (non V50-OKS) culture was similar to the Mock-SW480 in morphology. During the 17 days after transduction, the non-V50-OKS maintained their spindle-shaped morphology (FIG. 2A) and did not produce any V50 cells (FIG. 2B). In contrast, the V50-OKS gave rise to spindle shaped cells as well as dome-shaped colonies and also gave rise to nonV50 cells as well as around 10% of V50 cells. The cell was named secondary V50 ($2^{nd}$ V50) (FIG. 2B left panel, 2C). The $2^{nd}$ V50 cells formed dome-shaped colonies (FIG. 2B right panel). The $2^{nd}$ V50-OKS-cells exhibited CSC properties in terms of higher mRNA expression levels of the previously-reported marker genes: ABCG2 and LGR5 (Ding X. W. et al., Life Sci 2010; 86:631-7, Schepers A. G. et al., Science 2012; 337:730-5) (FIG. 2D), a higher percentage of the cells in the G1/G0 phase (FIG. 2E) and resistance to 5-FU (FIG. 2F).

Taken together, OKS-SW480 showed phenotypes which were similar to those described in the previous report (non-patent document 3) using O+S+K-SW480, thereby indicating that iCSCs identified as V50- and $2^{nd}$ V50-OKS-SW480 cells can be generated by using the polycistronic expression system, and that a uniform iCSC population into which all 3 factors have been introduced can be produced by using the polycistronic expression system.

Example 2: Verification of Tissue Reconstructing Ability of iCSCs In Vitro

It has previously been reported that CSCs had a high ability to form spheres when cultured in low attachment dishes with serum-free medium (Ricci-Vitiani L. et al., Nature 2007; 445:111-51, Sato T. et al., Gastroenterology 2011; 141:1762-72). To examine the sphere forming ability of these cells, a sphere formation assay was performed.

Consistent with the previous report (non-patent document 3) on colon iCSC using O+S+K-SW480, an obviously increased number of the spheres in $2^{nd}$ V50-OKS cells was observed, whereas it was hard to find any spheres in parental SW480 (FIG. 3A). The number of spheres was an intermediate level in the non-V50 cells from $1^{st}$ V50-OKS cells (FIG. 3A).

The previous xeno-transplantation experiments demonstrated that the colon iCSCs, but not the parental cell line, were able to reconstitute tissues in vivo that resembled actual human colon cancer tissues in terms of their immunohistological findings (non-patent document 3). However, it was still unclear whether the colon iCSCs could also show the same phenomenon in vitro. Thus, the spheres derived from parental SW480 cells and $2^{nd}$ V50-OKS cells were immunohistologically evaluated. The spheres derived from $2^{nd}$ V50-OKS cells were positive for CK20 and CDX2, and negative for CK7 (FIG. 3B), which are the consistent staining patterns for typical colon cancer tissues (B ayrak R et al., Diagn Pathol 2012; 7:9), whereas those from parental SW480 cells were negative for CK20 (FIG. 3B), indicating that the colon iCSCs-derived tissues not only in vivo, but also in vitro are able to recapitulate human colon cancer tissues, and that the tissue reconstructing ability is cancer stem cell specific. It is therefore considered it is possible to assess the sphere forming ability as a measure of the tissue reconstructing ability of these iCSCs.

It is known that human colon cancer tissues consist of not only cancer cells but also interstitial cells, such as vascular and mesenchymal cells (Takebe T. et al., Cell Stem Cell 2015; 16:556-65, Plaks V. et al., Cell Stem Cell 2015; 16:225-38). It was therefore investigated whether colon iCSCs were able to assemble more realistic colon cancer organoid in vitro with interstitial cells when cultivated with mesenchymal stem cells (MSCs) and human umbilical vein endothelial cells (HUVECs).

Figure 4:
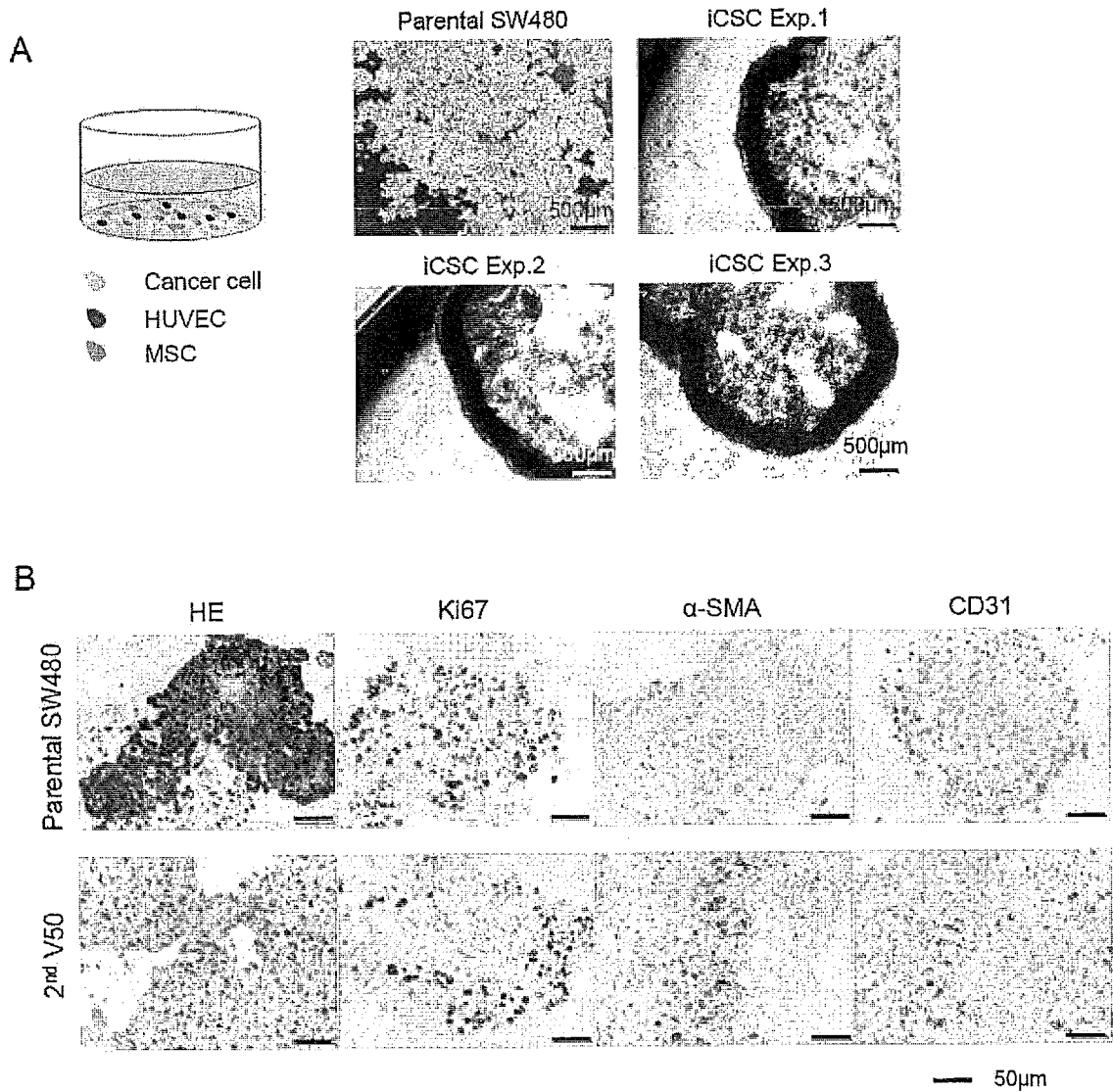
FIG. 4 (A) The spheres derived from iCSCs, but not parental SW480, became a colony of collective cells in co-culture with HUVECs and MSCs. (B) Histological and immunohistochemical analyses in the co-cultured spheres are shown. The spheres derived from iCSC, HUVECs and MSCs were positive for α-SMA and CD31, and only the outside of the spheres were positive for Ki67. The spheres derived from parental SW480, HUVECs and MSCs were negative for α-SMA and CD31, and were positive for Ki67 on the whole.

The $2^{nd}$ V50-OKS cells, but not parental SW480 cells, co-cultured with MSCs and HUVECs resulted in large aggregated collective cells (FIG. 4A). An immunohistochemical analysis was performed, and it was observed α-SMA and CD31, markers of myofibroblasts, which could be derived from MSCs (Quante M. et al., Cancer Cell 2011; 19:257-72), and vascular cells respectively, in the spheres derived from $2^{nd}$ V50-OKS cells, but not in those from parental SW480 cells (FIG. 4B). This showed that only iCSCs are able to assemble tissues with HUVECs and MSCs, and thus lead them to a mature stage.

Example 3: Comparison of the Gene Expression Profiles in Mock-SW480 Cells, Non-V50 Cells and $2^{nd}$ V50 OKS Cells To identify the molecular mechanisms that promote the properties of CSCs, the comprehensively gene expression patterns of Mock-SW480 cells, non-V50 cells from $1^{st}$ V50-OKS cells, and $2^{nd}$ V50-OKS cells 5 days after being sorted by a microarray were compared. First, the gene expression between Mock-SW480 and $2^{nd}$ V50-OKS cells was compared, and 3914 probes were identified with significant differences in their expression (t-test, false discovery rate (FDR)<0.05 and two fold differences) (FIG. 5A). Next, the gene expression profiles of $2^{nd}$ V50-OKS cells was compared with those of non-V50 cells from $1^{st}$ V50-OKS cells. It was identified that only 56 probes showed a Fold Chang>2, with an FDR<0.05 (FIG. 5B). Next, Venn diagrams was drawn of the probes that were more highly expressed in $2^{nd}$ V50 than non-V50, mock, and less expressed in $2^{nd}$ V50 than non-V50, mock, then 8 probes which overlapped in the Venn diagrams (FIG. 5C) was selected. Of these 8 probes were narrowed down to 3 probes, including semaphorin 6A (SEMA6A), a family with a sequence similarity 105 member A (FAM105A), and a regulator of calcineurin 2 (RCAN2), which moved in parallel to the ability of sphere formation in each cell (FIG. 5D, 5E).

SEMA6A is one of the semaphorin families that play a role in many developmental processes outside of the nervous system (Luo Y. et al., Cell 1993; 75:217-27). In addition to these normal functions of the semaphorins, many semaphorins have been found to have a functional activity associated with tumor progression (Neufeld G. et al., Cold Spring Harb Perspect Med 2012; 2:a006718, Worzfeld T. et al., Nat Rev Drug Discov 2014; 13:603-21). So far, little has been reported about FAM105A, but FAM105A has a conserved protein domain of Rho-GAP (Marchler-Bauer A. et al., Nucleic Acids Res 2015; 43:D222-6), that might regulate the Rho G protein. RCAN2 was originally identified as a thyroid hormone-responsive gene, ZAKI-4, from human fibroblasts (Miyazaki T. et al., J Biol Chem 1996; 271: 14567-71), and subsequently it was reported to function as a negative regulator of calcineurin (Cao X., et al., Biochem J 2002; 367:459-66).

Next, it was decided to perform experiments using small compounds acting on SEMA6A, FAM105A or RCAN2, or their target molecules. However, neither agonist nor antagonist for SEMA6A was, as far as search was conducted, commercially available, and the function of FAM105A was thus unclear. In contrast, RCAN2 are known to negatively regulate calcineurin, and calcineurin-NFAT (nuclear factor of activated T cells) signaling inhibitors such as FK506, which are theoretically presumed to have the same effect as RCAN2 on the colon iCSCs, were commercially available. Therefore focus was placed on evaluating the effects of FK506 on the properties of colon iCSCs.

Example 4: Verification of Effect on Maintenance and Expansion of iCSC by Calcineurin Inhibition (Flat Plane Adhesion Culture)

FK506 significantly reduced the number of cells in parental SW480 cultures, which is compatible with the reports that the blockade of calcineurin inhibits colon cancer cell line proliferation in vitro (Peuker K. et al., Nat Med 2016; 22:506-15). On the other hand, no significant effect of FK506 on the cell number was observed in the $2^{nd}$ V50-OKS cultures (FIG. 7A) (5 days after passage ±FK506 addition). In addition, the distinctively observed morphology, or dome-shaped colonies in $2^{nd}$ V50-OKS cells became more prominent with FK506, whereas the cell morphologies of parental SW480 did not change with FK506 (FIG. 7B). These data suggested that FK506 differentially acts on the colon iCSCs and the parental SW480 cells.

Figure 8:
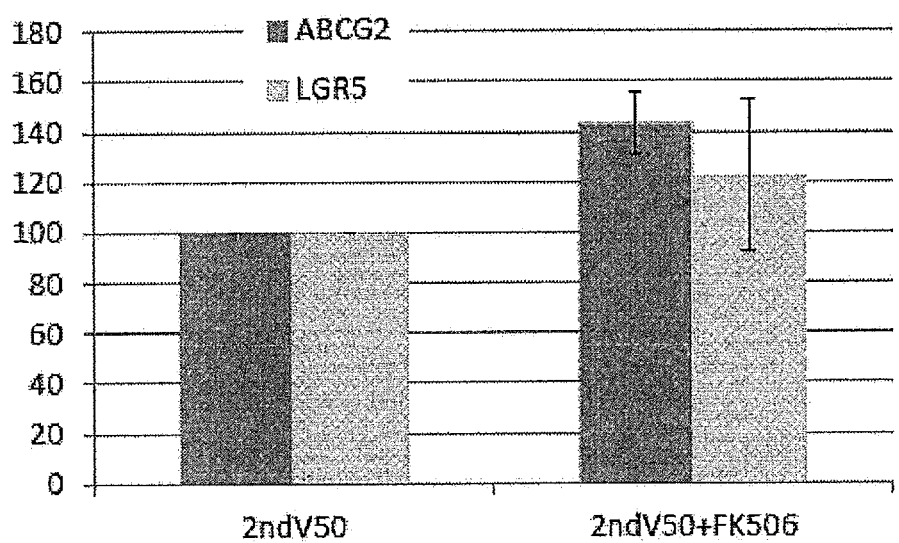
FIG. 8 shows that FK506 increases the expression level of stem cell marker in flat plane adhesion culture of induced colon cancer stem cell. The expression level of stem cell markers (ABCG2, LGR5) by administration of FK506 in induced colon cancer stem cells ($2^{nd}$ V50 cells) subjected to adhesion culture was compared by quantitative RT-PCR. N=3 Error bars are SD value (5 days after passage ±FK506 addition).

In addition, the expression levels of colon cancer stem cell markers (ABCG2, LGR5) were compared using quantitative RT-PCR for $2^{nd}$ V50 cells collected on day 5 after passage with or without addition of FK506. As a result, FK506 was shown to increase the expression of colon cancer stem cell marker (FIG. 8).

Furthermore, when $2^{nd}$ V50 cells were adhesion cultured with the addition of FK506, the total cell number was amplified to about 100 times in 10 days and about 1000 times in 15 days (FIG. 9, upper figure). During this time, the morphological characteristics of CSC were well maintained compared to the conditions without addition of FK506 (emergence of spindle-shaped flat cells was small, and a cell population mainly composed of characteristic colonies was maintained).

From the above, it was shown that inhibition of calcineurin with FK506 permits maintenance and expansion of iCSC.

Figure 7:
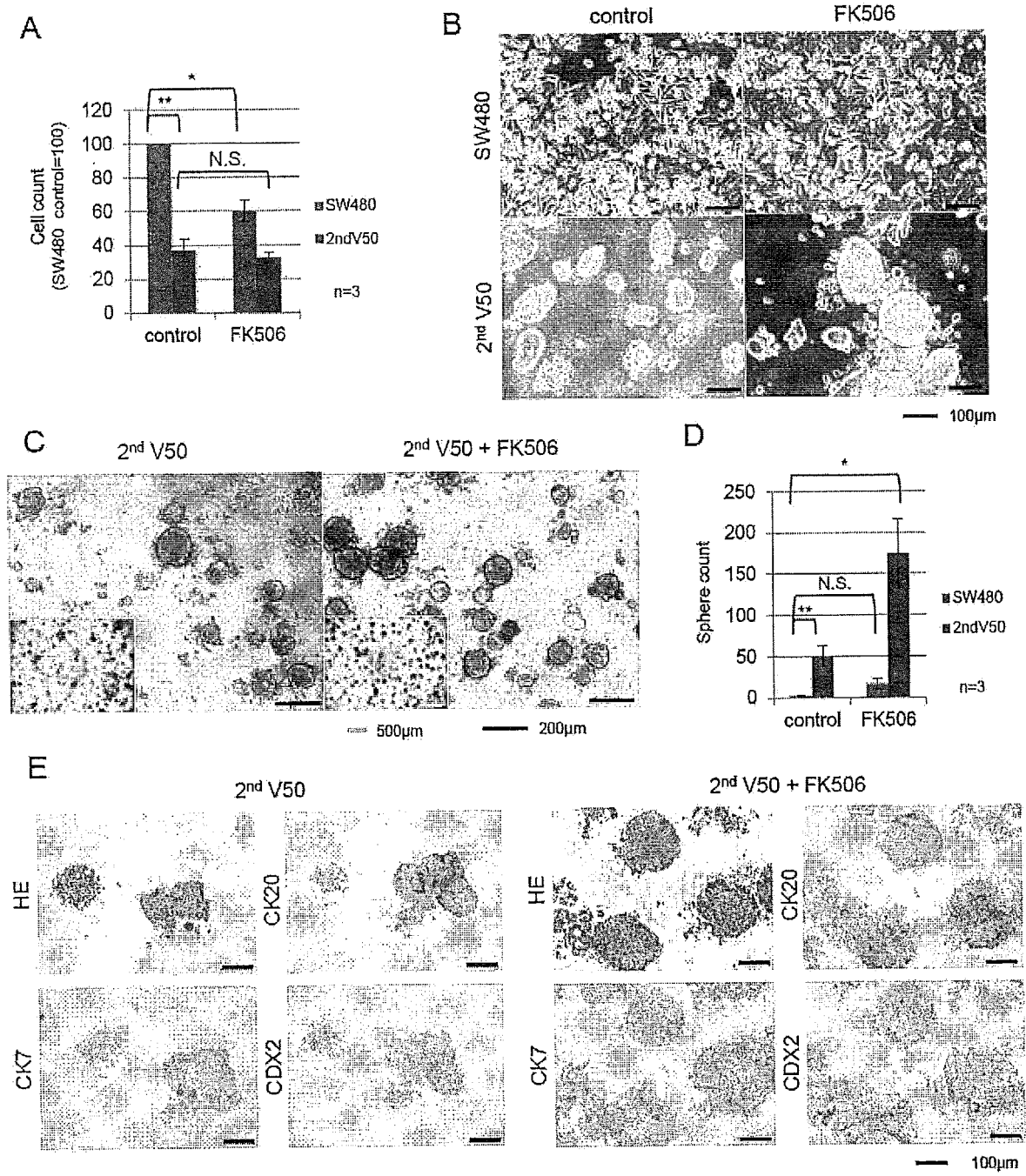
FIG. 7 (A) The cell number of parental SW480 cells and $2^{nd}$ V50-OKS cells with or without FK506 were counted 5 days after being plated (n=3). * P<0.05, ** P<0.01 (B) The morphological changes of parental SW480 cells and $2^{nd}$ V50-OKS cells with or without FK506 are shown. (C) The sphere forming ability of the $2^{nd}$ V50-OKS cells with or without FK506 is shown. Increased numbers of spheres were formed in the $2^{nd}$ V50-OKS cells with FK506. (D) The sphere count in parental SW480 cells or $2^{nd}$ V50-OKS cells with or without FK506 10 days after plated is shown (n=3). * p<0.05, ** p<0.01 (E) Histological and immunohistochemical analyses in the spheres of iCSCs with or without FK506 are shown. Both spheres were positive for CK20, CDX2 and negative for CK7.
Figure 10:
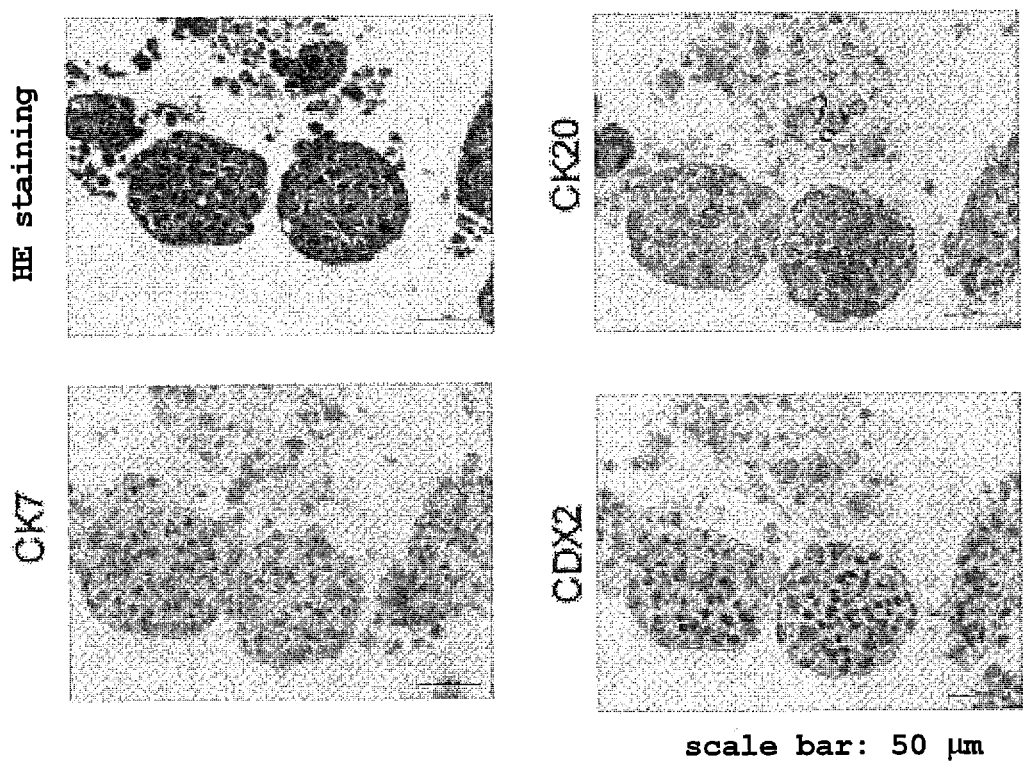
FIG. 10 The sphere formed from induced colon cancer stem cell added with FK506 and expanded shows the same immunostaining pattern as typical human colon cancer tissue. The HE staining and immunostaining of sphere (day 7) formed from $2^{nd}$ V50 cells expanded for 15 days in flat plane adhesion culture in the presence of FK506 (25 µM) are shown. CK20 positive, CK7 negative, CDX2 positive, typical human colon cancer tissue patterns are shown.

Example 5: Verification of Effect of Inhibition of Calcineurin on Sphere Forming Ability of iCSC The sphere forming ability was evaluated as an index of the tissue reconstructing ability of colon iCSC with or without FK506. FK506 significantly increased the number of spheres in $2^{nd}$ V50-OKS cells, but not in parental SW480 cells (FIGS. 7C, 7D). By immunohistochemical analysis, the spheres of $2^{nd}$ V50-OKS cells treated with FK506 were positive for CK20 and CDX2, negative for CK7, and had the same pattern as that of the spheres without FK506 (FIG. 7E). In addition, $2^{nd}$ V50 cells that had been cultured for 15 days in the presence of FK506 were then suspension cultured for 7 days to form spheres. As a result, similar to FIG. 7, the spheres of $2^{nd}$ V50 cells were positive for CK20 and CDX2, and negative for CK7 (FIG. 10).

Figure 11:
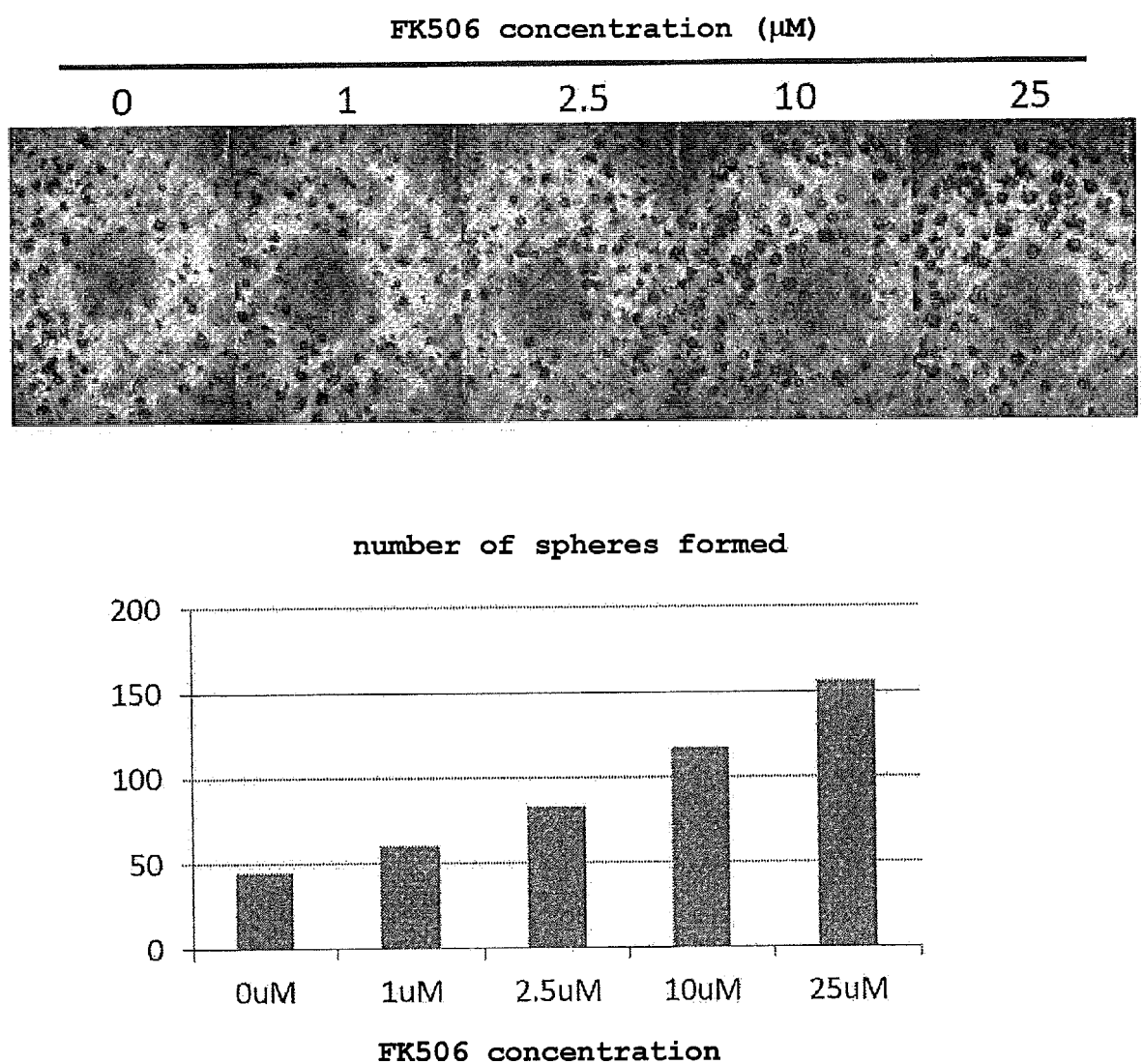
FIG. 11 The effect of FK506 addition on induced colon cancer stem cell is observed in a concentration range of at least 1 µM-25 µM. Upper Figure: The sphere formation experiment was performed by adding each concentration of FK506 shown in the Figure. Phase contrast micrograph Lower Figure: Number of spheres under each condition.

The sphere formation assay was performed by suspension culture of $2^{nd}$ V50-OKS cells without adding FK506 (0 µM), or adding FK506 at a concentration of 1 µM, 2.5 µM, 10 µM, or 25 µM for 10 days. As a result, the effect of the addition of FK506 on the sphere forming ability of colon iCSC was observed in a concentration range of at least 1 µM-25 µM (FIG. 11).

$2^{nd}$ V50 cells expansion cultured for 15 days in adhesion culture in the presence of FK506 (25 µM) were subjected to a sphere formation experiment for 10 days with or without addition of FK506.

Figure 12:
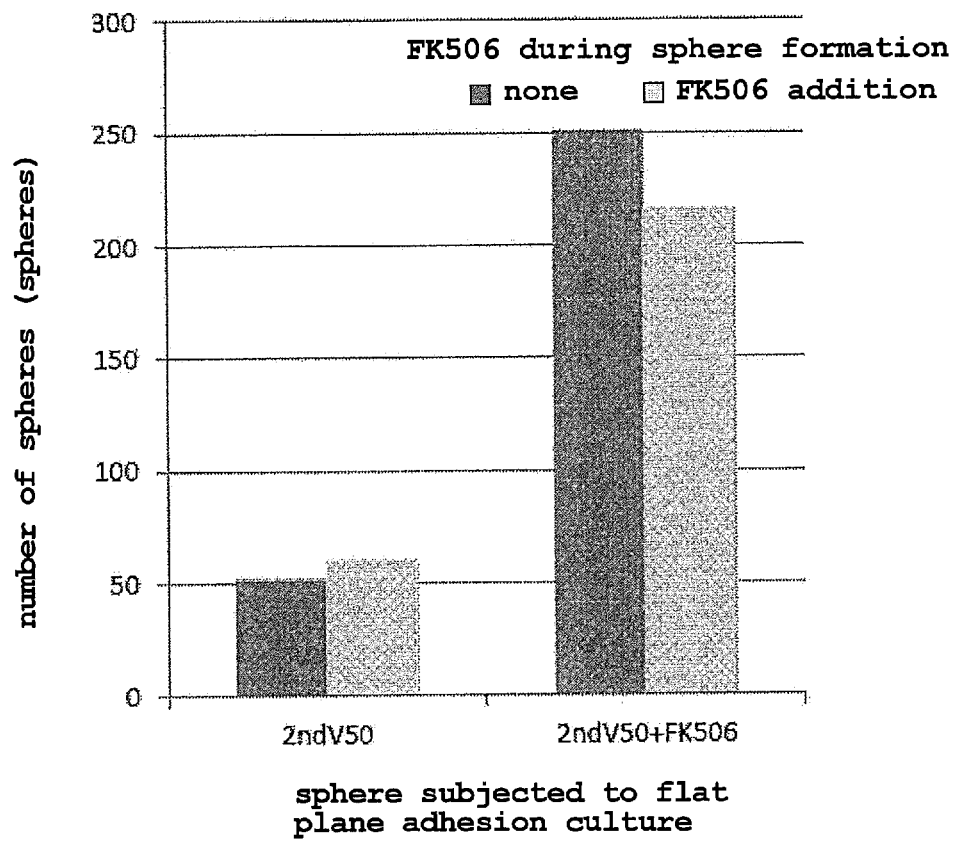
FIG. 12 Induced colon cancer stem cell added with FK506 and adhesion cultured shows high sphere forming ability.

As a result, it was demonstrated that, by adding FK506 at least during adhesion culture, colon iCSCs shows high sphere forming ability even without addition of FK506 during suspension culture (FIG. 12).

From the above, it was shown that inhibition of calcineurin with FK506 promotes sphere formation of colon iCSC, that is, the tissue reconstructing ability of colon iCSC can be enhanced.

Figure 13:
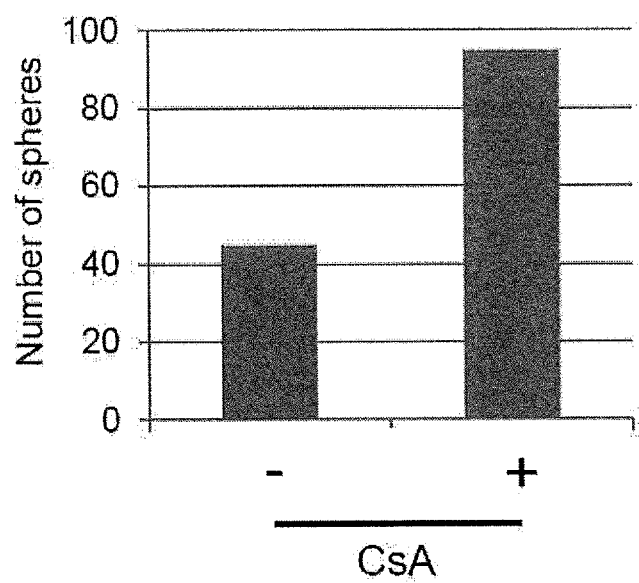
FIG. 13 shows the number of spheres after incubating $2^{nd}$ V50-OKS cells for 10 days without adding CsA (−) or adding 1 µM CsA (+).

In addition, a sphere formation assay was performed using another calcineurin inhibitor, cyclosporin A (CsA). $2^{nd}$ V50-OKS cells were cultured by suspension culture for 10 days without adding CsA (−), or with addition of 1 µM CsA (+). As a result, promotion of the sphere forming ability of colon iCSC was also observed by the addition of CsA (FIG. 13). Therefore, it is strongly suggested that the tissue reconstructing ability of colon iCSC can be similarly enhanced regardless of the kind of the inhibitor as long as it inhibits calcineurin.

Reference Example 1: Verification of Effect of GSK3 Inhibition on iCSC

Calcineurin has been reported to promote nuclear translocation of NFAT in other cells. Conversely, GSK3 was known as a molecule that promotes transfer of NFAT from the nucleus to the cytoplasm. Therefore, the present experiment was conducted under the hypothesis that inhibition of GSK3 on colon cancer stem cells would afford an effect opposite to that of calcineurin inhibitor FK506.

Figure 14:
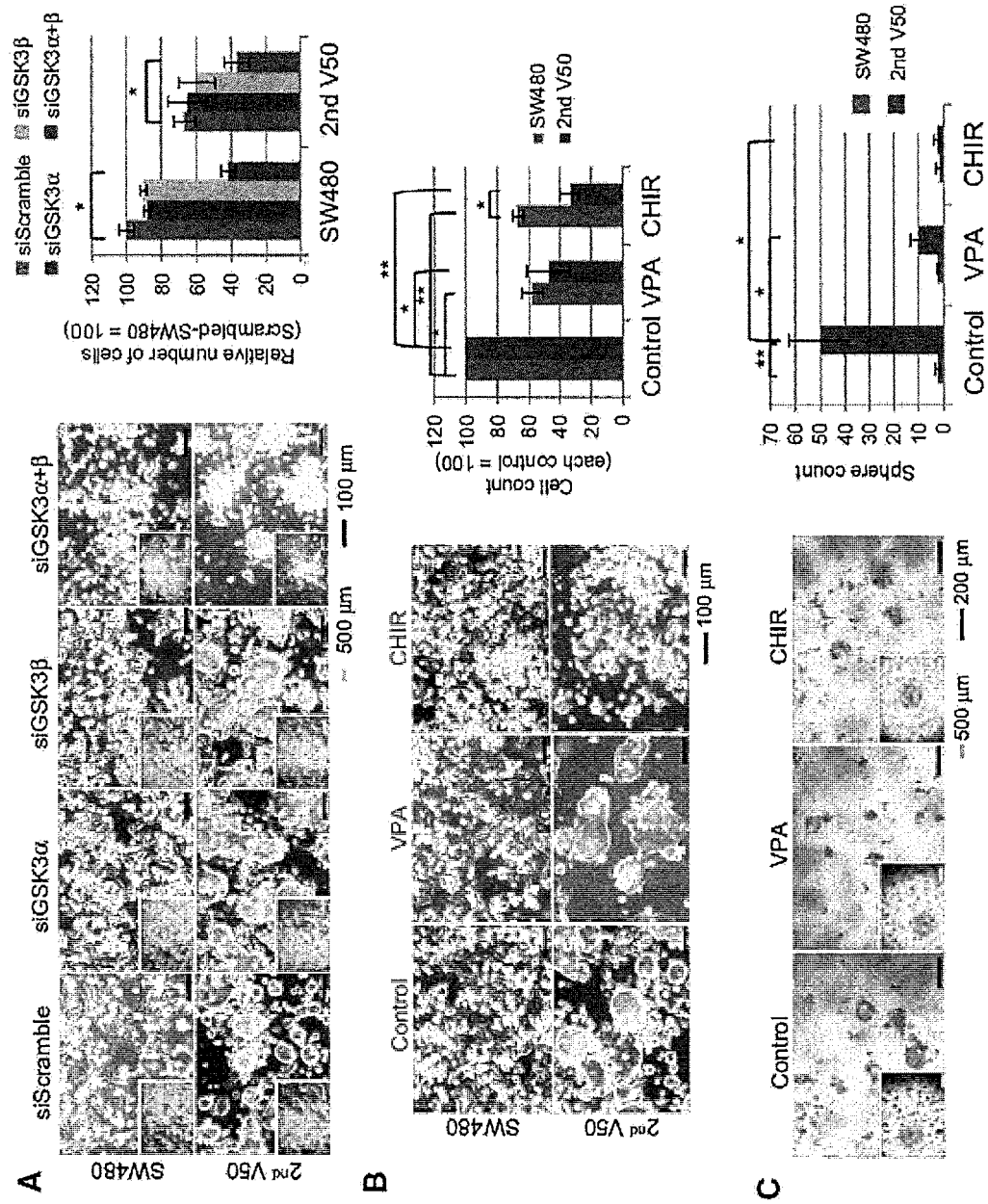
FIG. 14 shows that GSK3 inhibition suppresses the ability of induced colon cancer stem cell. (A) shows the effect of addition of siRNA on GSK3α and GSK3β in flat plane adhesion culture. (B) shows the effect of addition of valproic acid (VPA) or CHIR99021 in flat plane adhesion culture. (C) shows the effect of addition of valproic acid (VPA) or CHIR99021 (CHIR) on the sphere forming ability.

First, GSK3 was inhibited using siRNA against GSK3α and GSK3β. As a result, by adding both siRNA against GSK3α and siRNA against GSK33 in flat plane adhesion culture, the morphological characteristics (dome-shaped colonies) of iCSC were suppressed and flattened, and the number of cells also decreased (FIG. 14A). No effect was seen with a single siRNA, which suggests functional redundancy between GSK3α and GSK3β in colon cancer.

Next, it was examined whether addition of valproic acid (VPA) or CHIR99021 (CHIR), which are inhibitors of both GSK3α and β, had the same effect as siRNA. As a result, as shown in FIG. 14B, all GSK3 inhibitors showed the same effect as siRNA. Furthermore, similar to Example 4, the effects of these inhibitors on the sphere forming ability were examined, and all GSK3 inhibitors significantly suppressed the sphere forming ability of colon iCSC ($2^{nd}$ V50). What should be noted is that the sphere forming ability, which is a measure of tissue reconstructing ability of iCSC in $2^{nd}$ V50-OKS cells, was significantly suppressed by the addition of VPA and CHIR (FIG. 14C).

Figure 15:
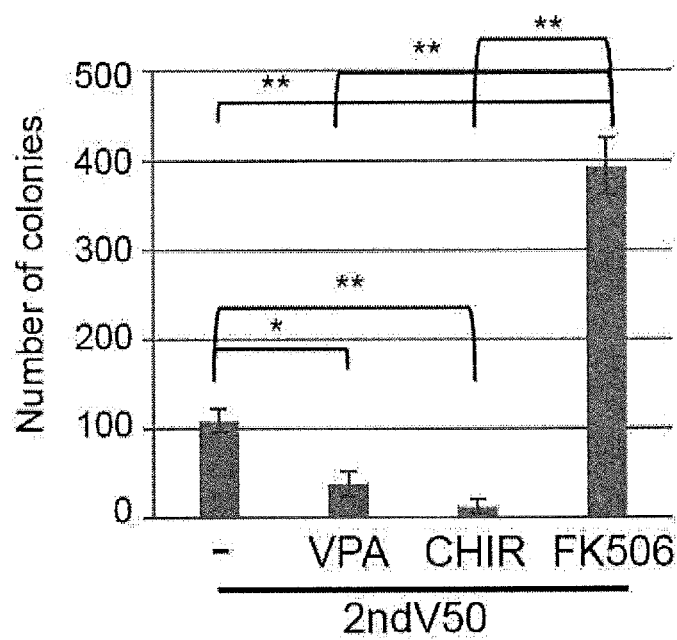
FIG. 15 shows the results of colony formation assay. The number of colonies formed from $2^{nd}$ V50-OKS cells treated with 1 mM VPA, 3 µM CHIR or 25 mM FK506, and $2^{nd}$ V50-OKS cells not treated with compound (n=3) is shown. * p<0.05 ** p<0.01

Furthermore, in the colony formation assay using $2^{nd}$ V50 cells in vitro, the number of secondary dome-shaped colonies decreased with VPA and CHIR99021, and increased with FK506 (FIG. 15). This result shows that these compounds affect self-replication of iCSC.

Reference Example 2: Localization of NFAT in $2^{nd}$ V50-OKS Cell

Figure 16:
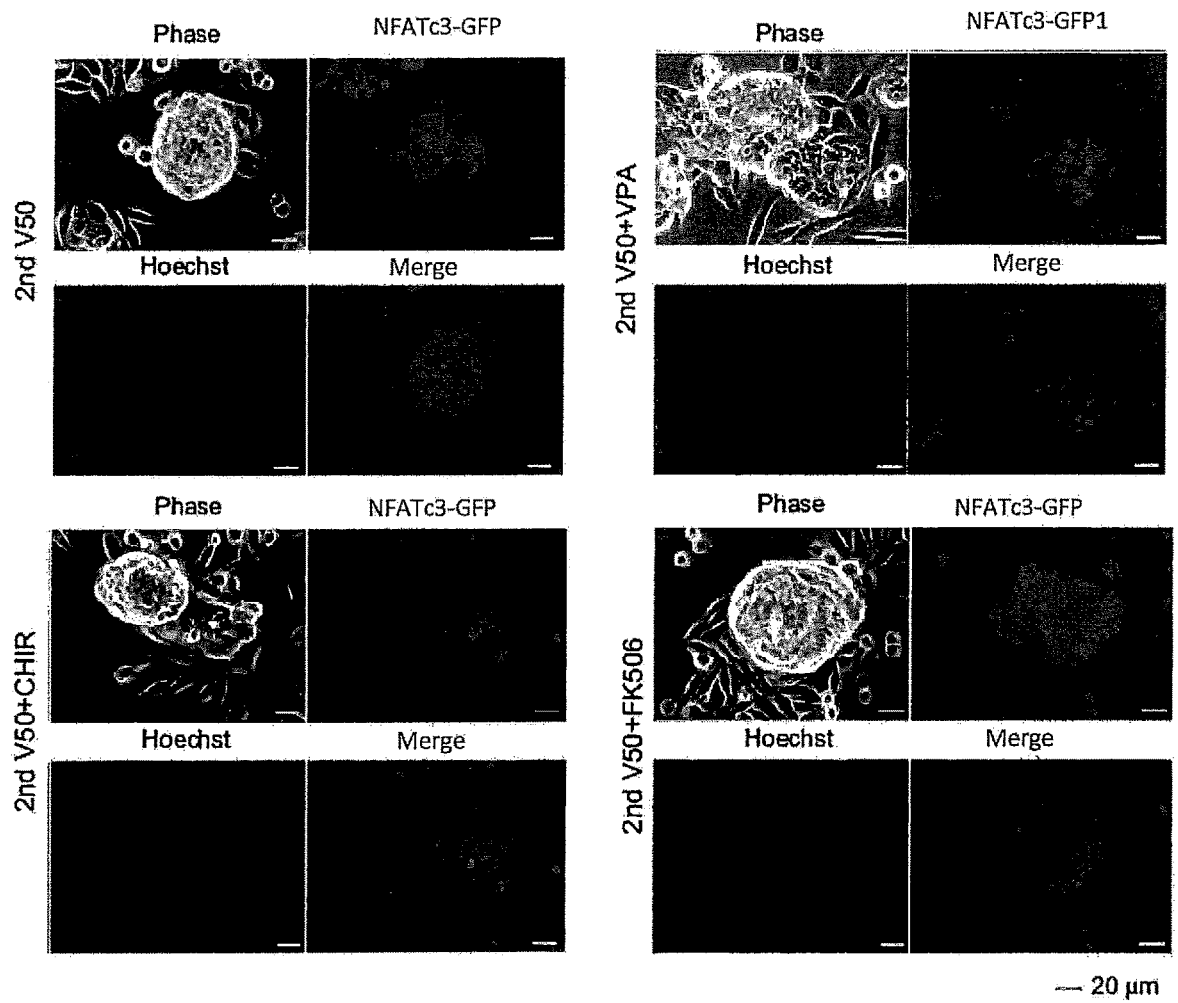
FIG. 16 shows localization of NFATc3 in $2^{nd}$ V50-OKS cells. Intracellular localization of NFATc3-GFP in $2^{nd}$ V50-OKS cells not treated with compound or treated with VPA, CHIR or FK506 is shown. NFATc3-GFP was confirmed in the nucleus when VPA and CHIR were used, and was confirmed in the cytoplasm when FK506 was used or when compound was not used.
Figure 17:
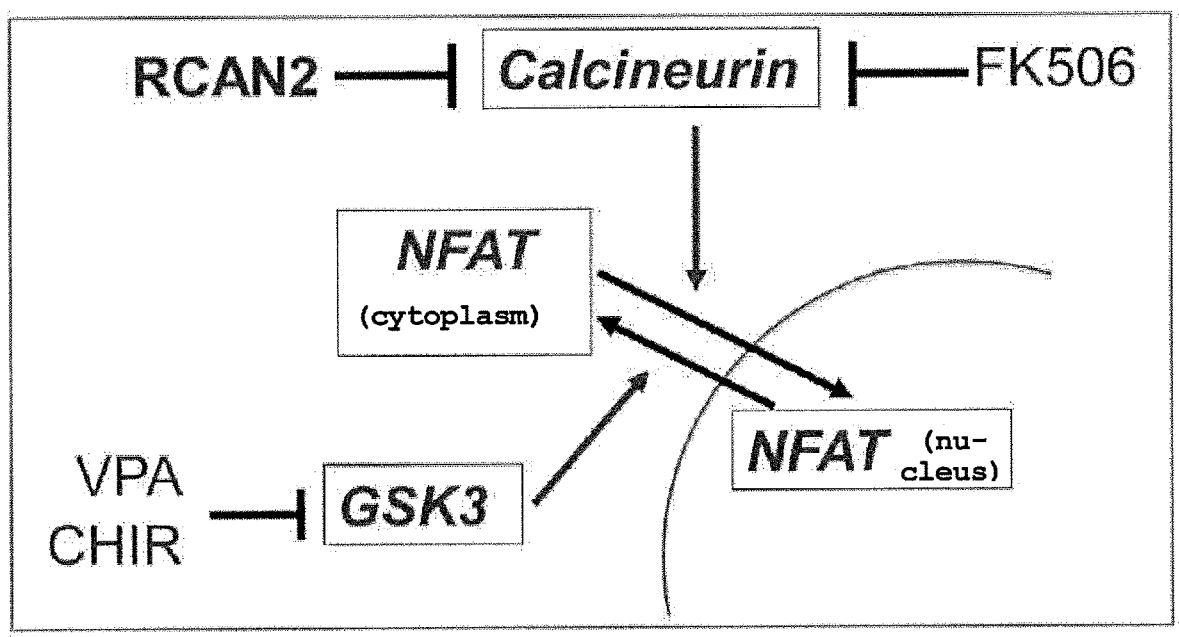
FIG. 17 is a reference diagram showing the relationship between each compound (FK506, VPA, CHIR99021) and each protein (NFAT, calcineurin, GSK3, RCAN2) when focusing on localization of NFAT.

Finally, the cellular localization of NFAT after the treatment of FK506, VPA and CHIR in the iCSCs was examined. NFATc3 fused to green fluorescent protein (NFATc3-GFP; Aramburu J, et al., Science, 1999; 285:2129-33, Peuker K, et al., Nat Med, 2016, 22:506-15) was retrovirally introduced into $2^{nd}$ V50-OKS cells. In the $2^{nd}$ V50-OKS cells without any compounds and those with FK506, it was observed that NFATc3-GFP localized in the cytoplasm. In contrast, localization of NFATc3-GFP was found in the nuclei of the $2^{nd}$ V50-OKS cells treated with VPA and CHIR (FIG. 16). These results suggest that inhibition of GSK3 affects iCSC. This is opposite to inhibition of calcineurin via cytoplasm-nuclear translocation of NFAT. The results support Reference Figure shown in FIG. 17.

This application is based on a patent application No. 2017-110626 filed in Japan (filing date: Jun. 5, 2017), the contents of which are incorporated in full herein.

INDUSTRIAL APPLICABILITY

According to the present invention, colon cancer stem cell or colon cancer organoid can be obtained in a large amount, which is extremely useful for application to screening for an anticancer agent and the like.

The invention claimed is:

1. A method for increasing the number of induced colon cancer stem cells derived from SW480 colon cancer cells, comprising:
   providing a population of induced colon cancer stem cells derived from SW480 colon cancer stem cells,
   contacting the population of the induced colon cancer stem cells with a calcineurin inhibitor at a concentration sufficient to induce colon cancer stem cell formation for a period of 5-25 days,
   wherein the induced colon cancer stem cells are adhesion cultured,
   thereby increasing the number of induced colon cancer stem cells as compared to culturing the induced colon cancer stem cells in the same manner except for the absence of the calcineurin inhibitor.

2. The method according to claim 1, wherein the induced colon cancer stem cells are induced by culturing the SW480 colon cancer cells, into which an exogenous reprogramming factor has been introduced, under conditions that promote reprogramming of the SW480 colon cancer cells to induced colon cancer stem cells.

3. The method according to claim 1 further comprising a step of three-dimensional culturing the induced colon cancer stem cells.

4. The method according to claim 3, wherein the three-dimensional culture step is performed after the step of adhesion-culturing the induced colon cancer stem cells.

5. The method according to claim 4, wherein the three-dimensional culture step is performed in the presence of the calcineurin inhibitor.

6. The method according to claim 3, wherein the three-dimensional culture step is performed by coculturing the induced colon cancer stem cells with a mesenchymal stem cell and a vascular endothelial cell.

7. The method according to claim 1, wherein the calcineurin inhibitor is FK506.

8. A method for forming an induced colon cancer organoid comprising:
   (a) inducing colon cancer stem cells derived from SW480 colon cancer cells by reprogramming the SW480 colon cancer cells to form a population of induced colon cancer stem cells, wherein the induced colon cancer stem cells are adhesion cultured,
   (b) sorting the induced colon cancer stem cells to obtain an enriched population of induced colon cancer stem cells,
   (c) coculturing the induced colon cancer stem cells with mesenchymal stem cells and vascular endothelial cells to establish a coculture population, wherein the coculturing is performed in three-dimensions, and wherein the coculturing is performed after adhesion culturing, and
   (d) contacting the coculture population with a calcineurin inhibitor at a concentration sufficient to induce colon cancer stem cell organoid formation for a period of 5-25 days, wherein the contacting is performed under culture conditions sufficient for establishing an induced colon cancer stem cell organoid.

9. The method according to claim 8, wherein the induced colon cancer stem cells are induced by culturing the SW480 colon cancer cells, into which an exogenous reprogramming factor has been introduced, under conditions that promote reprogramming of the SW480 colon cancer cells to induced colon cancer stem cells.

10. The method according to claim 8, wherein the calcineurin inhibitor is FK506.

* * * * *

SEQUENCE LISTING

<160> NUMBER OF SEQ ID NOS: 25

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
agccacatcg ctcagacac                                        19

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
gcccaatacg accaaatcc                                        19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gcgactatgc acaacgagag                                       20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cagtttgaat gcatgggaga                                           20

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
catgccagag gagcccaagc caaagagggg                                30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cgcaggtgtg ccttgagatg ggaactcttt                                30

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
ttcacatgtc ccagcactac caga                                      24

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
tcacatgtgt gagaggggca gtgtgc                                    26

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cacaaggaaa caccaatggc t                                         21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
acagctcctt cagtaaatgc c                                         21

<210> SEQ ID NO 11
<211> LENGTH: 20
<212> TYPE: DNA

```
<213> ORGANISM: Artificial Sequence
<220> FEATURE:
<223> OTHER INFORMATION: Primer

<400> SEQUENCE: 11
gatgttgctc agggtggact                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tttcccgcaa gacgtaactc                                              20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aggaatgctg gactggaagc                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ggtcgtggcc tttgaggtaa                                              20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ggcacaagct gaaatggtgg                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcagcttgtt acggggtgtc                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
caaactgcac ttggctccac                                              20
```

```
<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cacttggggt ggactcagtc                                              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aaggctctcc ccactagagg                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gaggagggat gagaatggcg                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gcagcaaggt gacaacagtg                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ttgatggcga ccagttctcc                                              20

<210> SEQ ID NO 23
<211> LENGTH: 25
<212> TYPE: RNA
<213> ORGANISM: Artificial Sequence
<220> FEATURE:
<223> OTHER INFORMATION: Synthetic siRNA sequence

<400> SEQUENCE: 23
ccaaggccaa guugaccauc ccuau                                        25

<210> SEQ ID NO 24
<211> LENGTH: 25
<212> TYPE: RNA
<213> ORGANISM: Artificial Sequence
<220> FEATURE:
```

-continued

```
<223> OTHER INFORMATION: Synthetic siRNA sequence

<400> SEQUENCE: 24
gcuccagauc augagaaagc uagau                                              25

<210> SEQ ID NO 25
<211> LENGTH: 25
<212> TYPE: RNA
<213> ORGANISM: Artificial Sequence
<220> FEATURE:
<223> OTHER INFORMATION: Synthetic siRNA sequence

<400> SEQUENCE: 25
aauucuccga acgugucacg ugaga                                              25
```